(12) United States Patent  
Dischert et al.

(10) Patent No.: US 9,506,093 B2  
(45) Date of Patent: Nov. 29, 2016

(54) RECOMBINANT MICROORGANISM FOR THE FERMENTATIVE PRODUCTION OF METHIONINE

(75) Inventors: Wanda Dischert, Vic-le-Comte (FR); Rainer Figge, Le Crest (FR)

(73) Assignee: METABOLIC EXPLORER, Saint-Beauzire (FR)

( * ) Notice: Subject to any disclaimer, the term of this patent is extended or adjusted under 35 U.S.C. 154(b) by 0 days.

(21) Appl. No.: 14/408,378

(22) PCT Filed: Jun. 18, 2012

(86) PCT No.: PCT/IB2012/001336  
§ 371 (c)(1),  
(2), (4) Date: Dec. 16, 2014

(87) PCT Pub. No.: WO2013/190343  
PCT Pub. Date: Dec. 27, 2013

(65) Prior Publication Data  
US 2015/0247175 A1    Sep. 3, 2015

(51) Int. Cl.  
*C12P 13/12*     (2006.01)  
*C12N 9/10*     (2006.01)

(52) U.S. Cl.  
CPC .............. *C12P 13/12* (2013.01); *C12N 9/1007* (2013.01); *C12Y 201/01014* (2013.01); *Y02P 20/52* (2015.11)

(58) Field of Classification Search  
CPC ................. C12P 13/12; C12N 9/1007; C12Y 201/01014  
See application file for complete search history.

(56) References Cited

U.S. PATENT DOCUMENTS

| | | |
|---|---|---|
| 7,611,873 B1 | 11/2009 | Usuda et al. |
| 7,790,424 B2 | 9/2010 | Park et al. |
| 8,252,555 B2 * | 8/2012 | Zelder ............... C12N 9/0091 435/113 |

FOREIGN PATENT DOCUMENTS

| | | |
|---|---|---|
| EP | 2726626 A1 | 5/2014 |
| JP | 00/157267 A | 6/2000 |
| WO | 02/10209 A1 | 2/2002 |
| WO | 2004/076659 A2 | 9/2004 |
| WO | 2005/007862 A2 | 1/2005 |
| WO | 2005/059093 A2 | 6/2005 |
| WO | 2005/059155 A2 | 6/2005 |
| WO | 2005/111202 A1 | 11/2005 |
| WO | 2006/008097 A2 | 1/2006 |
| WO | 2007/012078 A1 | 1/2007 |
| WO | 2007/077041 A1 | 7/2007 |
| WO | 2007/135188 A2 | 11/2007 |
| WO | 2009/043372 A1 | 4/2009 |
| WO | 2009/043803 A2 | 4/2009 |
| WO | 2009/144270 A1 | 12/2009 |
| WO | 2010/020681 A1 | 2/2010 |
| WO | 2011/073122 A1 | 6/2011 |
| WO | 2012/055798 A1 | 5/2012 |
| WO | 2012/090021 A1 | 7/2012 |

OTHER PUBLICATIONS

Written Opinion PCT/IB2012/001336 (Apr. 2005).*  
Anderson, "Growth Requirements of Virus-Resistant Mutants of *Escherichia coli* Strain "B"," 1946, Proc. Natl. Acad. Sci. USA 32:120-128.  
Bradford, "A Rapid and Sensitive Method for the Quantitation of Microgram Quantities of Protein Utilizing the Principle fo Protein-Dye Binding," 1976, Anal. Biochem. 72: 248-254.  
Carrier and Keasling, "Library of Synthetic 5' Secondary Structures to Manipulate mRNA Stability in *Escherichia coli*," 1999, Biotechnol. Prog. 15: 58-64.  
Datsenko and Wanner, "One-step inactivation of chromosomal genes in *Escherichia coli* K-12 unsing PCR products," 2000, Proc Natl Acad Sci U S A. 97: 6640-6645.  
Foster et al., "The Purification and Properties of a Factor containing Vitamine B12 concerned in the Synthesis of Methionine by *Escherichia coli*," 1961, Biochem. J. 80: 519-531.  
Gonzalez et al., "Comparison of Cobalamin-Independent and Cobalamin-Dependent Methionine Synthases from *Escherichia coli*: Two Solutions to the Same Chemical Problem," 1992, Biochemistry. 31: 6045-6056.  
Harrington, Laughlin and Liang, "Balanced branching in transcription termination," 2001 Proc Natl Acad Sci U S A. Apr. 24; 98(9):5019-24.  
Liebl et al., "Requirement of chelating coupunds for the growth of Corynebacterium glutamicum in synthetic media," 1989, Appl. Microbiol. Biotechnol. 32: 205-210.  
Norrander et al., "Contruction of improved M13 vectors using oligodeoxynucleotide-directed mutagenesis," 1983. Gene. 26: 101-106.  
Orosz et al., "Analysis of the complex transcription termination region of the *Escherichia coli* rrnB gene," 1991, Eur. J. Biochem. 201: 653-659.  
Riedel et al., "Characterization of the Phosphoenolpyruvate Carboxykinase Gene from Corynebacterium glutamicum and Significance of the Enzyme for Growth and Amino Acid Production," 2001, J. Mol. Microbiol. Biotechnol. 3: 573-583.  
Saunderson, "Comparative metabolism of L-methionine, DL-methionine and DL-2-hydroxy 4-methylthiobutanoic acid by broiler chicks," 1985 British Journal of Nutrition 54: 621-633.  
Schaefer et al., "Automated Sampling Device for Monitoring Intracellular Metabolite Dynamics," 1999, Anal. Biochem. 270: 88-96.

(Continued)

*Primary Examiner* — Tekchand Saidha  
(74) *Attorney, Agent, or Firm* — Birch, Stewart, Kolasch & Birch, LLP

(57) ABSTRACT

The present invention is related to a recombinant microorganism optimized for the fermentative production of methionine, wherein the activity of the cobalamin-independent methionine synthase MetE is attenuated in said microorganism. The invention is also related to a method for producing methionine by fermentation.

11 Claims, No Drawings

(56) References Cited

OTHER PUBLICATIONS

Hondorp et al., "Oxidation of Cysteine 645 of Cobalamin-Independent Methionine Synthase Causes a Methionine Limitation in *Escherichia coli*," 2009, Journal of Bacteriology, vol. 191, No. 10, pp. 3407-3410.
Kumar et al., "Methionine production by fermentation," 2005, Biochtechnology Advances, vol. 23, No. 1, pp. 41-61.
Chu J, et al., "Cloning and Expression of the metE Gene in *Escherichia coli*," 1985, Archives of Biochemistry and Biophysics, vol. 239, No. 2, pp. 467-474.
Aldea M et al., "Generation of a Detailed Physical and Genetic Map of the ilv-metE-udp Region of the *Escherichia coli* Chromosome," 1988, Journal of Molecular Biology, vol. 200, No. 3, pp. 427-438.
May 7, 2013 (WO) International Search Report—App. PCT/IB2012/001336.

* cited by examiner

SEQUENCE LISTING

<160> NUMBER OF SEQ ID NOS: 22

<210> SEQ ID NO 1
<211> LENGTH: 39
<212> TYPE: DNA
<213> ORGANISM: Artificial Sequence
<220> FEATURE:
<223> OTHER INFORMATION: Oligonucleotide

<400> SEQUENCE: 1
cgtaggcgcc ggtaccgagt gcagatcggc tggaaggcg                    39

<210> SEQ ID NO 2
<211> LENGTH: 115
<212> TYPE: DNA
<213> ORGANISM: Artificial Sequence
<220> FEATURE:
<223> OTHER INFORMATION: Oligonucleotide

<400> SEQUENCE: 2
gcttgtatac aacagataaa acgaaaggcc cagtctttcg actgagcctt tcgttttatt       60
tgatgcattt ctgtagaatt ttacacttat agtatcatta ctgattgaga cttca          115

<210> SEQ ID NO 3
<211> LENGTH: 108
<212> TYPE: DNA
<213> ORGANISM: Artificial Sequence
<220> FEATURE:
<223> OTHER INFORMATION: Oligonucleotide

<400> SEQUENCE: 3
agactgggcc tttcgtttta tctgttgtat acaagcttta cctagggccc ttaattaaat       60
aatgaataag ggtgtttaag taaaggaaaa catcaccgtt cctggcat                  108

<210> SEQ ID NO 4
<211> LENGTH: 42
<212> TYPE: DNA
<213> ORGANISM: Artificial Sequence
<220> FEATURE:
<223> OTHER INFORMATION: Oligonucleotide

<400> SEQUENCE: 4
cgtaggcgcc ggtacccagc ataatcattc accacacatc cg                         42

<210> SEQ ID NO 5
<211> LENGTH: 35
<212> TYPE: DNA
<213> ORGANISM: Artificial Sequence
<220> FEATURE:
<223> OTHER INFORMATION: Oligonucleotide

<400> SEQUENCE: 5
tcccccgggg tataccatat gaatatcctc cttag                                 35

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide

<400> SEQUENCE: 6
gcccaagctt tgtaggctgg agctgcttcg                                       30

<210> SEQ ID NO 7
<211> LENGTH: 39
<212> TYPE: DNA
<213> ORGANISM: Artificial Sequence
<220> FEATURE:
<223> OTHER INFORMATION: Oligonucleotide

<400> SEQUENCE: 7
cgtaggcctg ggcccgagct gttgacaatt aatcatccg                             39

<210> SEQ ID NO 8
<211> LENGTH: 79
<212> TYPE: DNA
<213> ORGANISM: Artificial Sequence
<220> FEATURE:
<223> OTHER INFORMATION: Oligonucleotide

<400> SEQUENCE: 8
cgaaggcctt taattaagca gaaaggccca cccgaaggtg agccaggcgg ccgcttactg       60
gtattcgcta atcggtacg                                                79

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide

<400> SEQUENCE: 9
cagaccaccc aactggcgac c                                             21

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
gccattggaa tcgaccagcc                                               20

<210> SEQ ID NO 11
<211> LENGTH: 134
<212> TYPE: DNA
<213> ORGANISM: Artificial Sequence
<220> FEATURE:
<223> OTHER INFORMATION: Oligonucleotide

<400> SEQUENCE: 11
tcggcgcctt aattaacatc aaataaaacg aaaggctcag tcgaaagact gggcctttcg   60
ttttatctgt ttacgtagag ctgttgacga ttaatcatcc ggctcgtata ctgtgtggaa  120
taaggaggta tatt                                                    134

<210> SEQ ID NO 12
<211> LENGTH: 62
<212> TYPE: DNA
<213> ORGANISM: Artificial Sequence
<220> FEATURE:
<223> OTHER INFORMATION: Oligonucleotide

<400> SEQUENCE: 12
ccagaactaa aattgaagat ttgagccata atatacctcc ttattccaca cagtatacga   60
gc                                                                  62

<210> SEQ ID NO 13
<211> LENGTH: 75
<212> TYPE: DNA
<213> ORGANISM: Artificial Sequence
<220> FEATURE:
<223> OTHER INFORMATION: Oligonucleotide

<400> SEQUENCE: 13
cccaagcttg catgcgctag cgagctcgag aaaggcccac ccgaaggtga gccaggttaa   60
ccgtgacggc gttcg                                                    75

<210> SEQ ID NO 14
<211> LENGTH: 94
<212> TYPE: DNA
<213> ORGANISM: Artificial Sequence
<220> FEATURE:
<223> OTHER INFORMATION: Oligonucleotide

```
<400> SEQUENCE: 14
tacgtagcta gcgagctgtt gacgattaat catccggctc gtatactgtg tggaataagg    60
aggtatatta tggcaaaggt atcgctggag aaag                                94

<210> SEQ ID NO 15
<211> LENGTH: 85
<212> TYPE: DNA
<213> ORGANISM: Artificial Sequence
<220> FEATURE:
<223> OTHER INFORMATION: Oligonucleotide

<400> SEQUENCE: 15
cccaagcttg catgccctag gtaaaaaaaa taagagttac catttaaggt aactcttatt    60
tttattagta cagcagacgg gcgcg                                          85

<210> SEQ ID NO 16
<211> LENGTH: 120
<212> TYPE: DNA
<213> ORGANISM: Artificial Sequence
<220> FEATURE:
<223> OTHER INFORMATION: Oligonucleotide

<400> SEQUENCE: 16
agaaacccgc gcggcactgg cgaacatggt gcaggcggcg cagaacttgc gtcggggta    60 aaatccaaac cgggtggtaa taccacccgg tcttttctca tgtaggctgg agctgcttcg   120

<210> SEQ ID NO 17
<211> LENGTH: 120
<212> TYPE: DNA
<213> ORGANISM: Artificial Sequence
<220> FEATURE:
<223> OTHER INFORMATION: Oligonucleotide

<400> SEQUENCE: 17
gcagaagatg gctggcagcg tatgctggaa tggtttaagc agtatggtgg gaagaagtcg    60
ctgtaagcag aaaggcccac ccgaaggtga gccagtgtga catatgaata tcctccttag   120

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide

<400> SEQUENCE: 18
cgtttgggac tggatgtgct gg                                             22

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide

<400> SEQUENCE: 19
gcgtggtacg gcaaactgac                                                20

<210> SEQ ID NO 20
<211> LENGTH: 2262
<212> TYPE: DNA
<213> ORGANISM: Escherichia coli

<400> SEQUENCE: 20
```

```
atgacaatat tgaatcacac cctcggtttc cctcgcgttg ccctgcgtcg cgagctgaaa      60
aaagcgcaag aaagttattg ggcggggaac tccacgcgtg aagaactgct ggcggtaggg     120
cgtgaattgc gtgctcgtca ctgggatcaa caaaagcaag cgggtatcga cctgctgccg     180
gtgggcgatt ttgcctggta cgatcatgta ctgaccacca gtctgctgct gggtaacgtt     240
ccggcgcgtc atcagaacaa agatggttcg gtagatatcg acaccctgtt ccgtattggt     300
cgtgacgtg cgccgactgg cgaacctgcg gcggcagcgg aaatgaccaa atggtttaac     360
accaactatc actacatggt gccggagttc gttaaaggcc aacagttcaa actgacctgg     420
acgcagctgc tggacgaagt ggacgaggcg ctggcgctgg ccacaaggt gaaacctgtg     480
ctgctggggc cggttacctg gctgtggctg gggaaagtga aggtgaaca atttgaccgc     540
ctgagcctgc tgaacgacat tctgccggtt tatcagcaag tgctggcaga actggcgaaa     600
cgcggcatcg agtgggtaca gattgatgaa cccgcgctgg tactggaact accacaggcg     660
tggctggacg catacaaacc cgcttacgac gcgctccagg acaggtgaa actgctgctg     720
accacctatt ttgaaggcgt aacgccaaat ctcgacacga ttactgcgct gcctgttcag     780
ggtctgcatg ttgacctcgt acatggtaaa gatgacgttg ctgaactgca caagcgcctg     840
ccttctgact ggttgctgtc tgcgggtctg atcaatggtc gtaacgtctg gcgcgccgat     900
cttaccgaga aatatgcgca aattaaggac attgtcggca aacgtgattt gtgggtggca     960
tcttcctgct cgttgctgca cagccccatc gacctgagcg tggaaacgcg tcttgatgca    1020
gaagtgaaaa gctggtttgc cttcgcccta caaaaatgcc atgaactggc actgctgcgc    1080
gatgcgctga acagtggtga cacggcagct ctggcagagt ggagcgcccc gattcaggca    1140
cgtcgtcact ctacccgcgt acataatccg gcggtagaaa agcgtctggc ggcgatcacc    1200
gcccaggaca gccagcgtgc gaatgtctat gaagtgcgtg ctgaagccca gcgtgcgcgt    1260
tttaaactgc cagcgtggcc gaccaccacg attggttcct tcccgcaaac cacggaaatt    1320
cgtaccctgc gtctggattt caaaaagggc aatctcgacg ccaacaacta ccgcacgggc    1380
attgcggaac atatcaagca ggccattgtt gagcaggaac gtttgggact ggatgtgctg    1440
gtacatggcg aggccgagcg taatgacatg gtggaatact ttggcgagca cctcgacgga    1500
tttgtcttta cgcaaaacgg ttgggtacag agctacggtt cccgctgcgt gaagccaccg    1560
attgtcattg gtgacattag ccgcccggca ccgattaccg tggagtgggc gaagtatgcg    1620
caatcgctga ccgacaaacc ggtgaaaggg atgctgacgg ggccggtgac catactctgc    1680
tggtcgttcc cgcgtgaaga tgtcagccgt gaaaccatcg ccaaacagat tgcgctggcg    1740
ctgcgtgatg aagtggccga tctggaagcc gctggaattg catcatcca gattgacgaa    1800
ccggcgctgc gcgaaggttt accgctgcgt cgtagcgact gggatgcgta tctccagtgg    1860
ggcgtagagg ccttccgtat caacgccgcc gtggcgaaag atgacacaca aatccacact    1920
cacatgtgtt attgcgagtt caacgacatc atggattcga ttgcggcgct ggacgcagac    1980
gtcatcacca tcgaaacctc gcgttccgac atggagttgc tggagtcgtt tgaagagttt    2040
gattatccaa atgaaatcgg tcctggcgtc tatgacattc actcgccaaa cgtaccgagc    2100
gtggaatgga ttgaagcctt gctgaagaaa gcggcaaaac gcattccggc agagcgcctg    2160
tgggtcaacc cggactgtgg cctgaaaacg cgcggctggc agaaacccg cgcggcactg    2220
gcgaacatgg tgcaggcggc gcagaacttg cgtcgggggt aa                      2262
```

<210> SEQ ID NO 21

<211> LENGTH: 753
<212> TYPE: PRT
<213> ORGANISM: Escherichia coli

<400> SEQUENCE: 21

```
Met Thr Ile Leu Asn His Thr Leu Gly Phe Pro Arg Val Gly Leu Arg
1               5                   10                  15

Arg Glu Leu Lys Lys Ala Gln Glu Ser Tyr Trp Ala Gly Asn Ser Thr
            20                  25                  30

Arg Glu Glu Leu Leu Ala Val Gly Arg Glu Leu Arg Ala Arg His Trp
        35                  40                  45

Asp Gln Gln Lys Gln Ala Gly Ile Asp Leu Leu Pro Val Gly Asp Phe
    50                  55                  60

Ala Trp Tyr Asp His Val Leu Thr Thr Ser Leu Leu Gly Asn Val
65                  70                  75                  80

Pro Ala Arg His Gln Asn Lys Asp Gly Ser Val Asp Ile Asp Thr Leu
                85                  90                  95

Phe Arg Ile Gly Arg Gly Arg Ala Pro Thr Gly Glu Pro Ala Ala Ala
            100                 105                 110

Ala Glu Met Thr Lys Trp Phe Asn Thr Asn Tyr His Tyr Met Val Pro
        115                 120                 125

Glu Phe Val Lys Gly Gln Gln Phe Lys Leu Thr Trp Thr Gln Leu Leu
    130                 135                 140

Asp Glu Val Asp Glu Ala Leu Ala Leu Gly His Lys Val Lys Pro Val
145                 150                 155                 160

Leu Leu Gly Pro Val Thr Trp Leu Trp Leu Gly Lys Val Lys Gly Glu
                165                 170                 175

Gln Phe Asp Arg Leu Ser Leu Leu Asn Asp Ile Leu Pro Val Tyr Gln
            180                 185                 190

Gln Val Leu Ala Glu Leu Ala Lys Arg Gly Ile Glu Trp Val Gln Ile
        195                 200                 205

Asp Glu Pro Ala Leu Val Leu Glu Leu Pro Gln Ala Trp Leu Asp Ala
    210                 215                 220

Tyr Lys Pro Ala Tyr Asp Ala Leu Gln Gly Gln Val Lys Leu Leu Leu
225                 230                 235                 240

Thr Thr Tyr Phe Glu Gly Val Thr Pro Asn Leu Asp Thr Ile Thr Ala
                245                 250                 255

Leu Pro Val Gln Gly Leu His Val Asp Leu Val His Gly Lys Asp Asp
            260                 265                 270

Val Ala Glu Leu His Lys Arg Leu Pro Ser Asp Trp Leu Leu Ser Ala
        275                 280                 285

Gly Leu Ile Asn Gly Arg Asn Val Trp Arg Ala Asp Leu Thr Glu Lys
    290                 295                 300

Tyr Ala Gln Ile Lys Asp Ile Val Gly Lys Arg Asp Leu Trp Val Ala
305                 310                 315                 320

Ser Ser Cys Ser Leu Leu His Ser Pro Ile Asp Leu Ser Val Glu Thr
                325                 330                 335

Arg Leu Asp Ala Glu Val Lys Ser Trp Phe Ala Phe Ala Leu Gln Lys
            340                 345                 350

Cys His Glu Leu Ala Leu Leu Arg Asp Ala Leu Asn Ser Gly Asp Thr
        355                 360                 365

Ala Ala Leu Ala Glu Trp Ser Ala Pro Ile Gln Ala Arg Arg His Ser
    370                 375                 380

Thr Arg Val His Asn Pro Ala Val Glu Lys Arg Leu Ala Ala Ile Thr
```

```
                385                 390                 395                 400
        Ala Gln Asp Ser Gln Arg Ala Asn Val Tyr Glu Val Arg Ala Glu Ala
                        405                 410                 415

Gln Arg Ala Arg Phe Lys Leu Pro Ala Trp Pro Thr Thr Ile Gly
                    420                 425                 430

Ser Phe Pro Gln Thr Thr Glu Ile Arg Thr Leu Arg Leu Asp Phe Lys
                    435                 440                 445

Lys Gly Asn Leu Asp Ala Asn Asn Tyr Arg Thr Gly Ile Ala Glu His
                    450                 455                 460

Ile Lys Gln Ala Ile Val Glu Gln Glu Arg Leu Gly Leu Asp Val Leu
        465                 470                 475                 480

Val His Gly Glu Ala Glu Arg Asn Asp Met Val Glu Tyr Phe Gly Glu
                        485                 490                 495

His Leu Asp Gly Phe Val Phe Thr Gln Asn Gly Trp Val Gln Ser Tyr
                    500                 505                 510

Gly Ser Arg Cys Val Lys Pro Pro Ile Val Ile Gly Asp Ile Ser Arg
                    515                 520                 525

Pro Ala Pro Ile Thr Val Glu Trp Ala Lys Tyr Ala Gln Ser Leu Thr
                    530                 535                 540

Asp Lys Pro Val Lys Gly Met Leu Thr Gly Pro Val Thr Ile Leu Cys
        545                 550                 555                 560

Trp Ser Phe Pro Arg Glu Asp Val Ser Arg Glu Thr Ile Ala Lys Gln
                        565                 570                 575

Ile Ala Leu Ala Leu Arg Asp Glu Val Ala Asp Leu Glu Ala Ala Gly
                    580                 585                 590

Ile Gly Ile Ile Gln Ile Asp Glu Pro Ala Leu Arg Glu Gly Leu Pro
                    595                 600                 605

Leu Arg Arg Ser Asp Trp Asp Ala Tyr Leu Gln Trp Gly Val Glu Ala
                    610                 615                 620

Phe Arg Ile Asn Ala Ala Val Ala Lys Asp Asp Thr Gln Ile His Thr
        625                 630                 635                 640

His Met Cys Tyr Cys Glu Phe Asn Asp Ile Met Asp Ser Ile Ala Ala
                        645                 650                 655

Leu Asp Ala Asp Val Ile Thr Ile Glu Thr Ser Arg Ser Asp Met Glu
                    660                 665                 670

Leu Leu Glu Ser Phe Glu Glu Phe Asp Tyr Pro Asn Glu Ile Gly Pro
                    675                 680                 685

Gly Val Tyr Asp Ile His Ser Pro Asn Val Pro Ser Val Glu Trp Ile
                    690                 695                 700

Glu Ala Leu Leu Lys Lys Ala Ala Lys Arg Ile Pro Ala Glu Arg Leu
        705                 710                 715                 720

Trp Val Asn Pro Asp Cys Gly Leu Lys Thr Arg Gly Trp Pro Glu Thr
                        725                 730                 735

Arg Ala Ala Leu Ala Asn Met Val Gln Ala Gln Asn Leu Arg Arg
                    740                 745                 750

Gly

<210> SEQ ID NO 22
<211> LENGTH: 152
<212> TYPE: PRT
<213> ORGANISM: Escherichia coli

<400> SEQUENCE: 22

Met Thr Ile Leu Asn His Thr Leu Gly Phe Pro Arg Val Gly Leu Arg
```

```
1               5                   10                  15
Arg Glu Leu Lys Lys Ala Gln Glu Ser Tyr Trp Ala Gly Asn Ser Thr
            20                  25                  30

Arg Glu Glu Leu Leu Ala Val Gly Arg Glu Leu Arg Ala Arg His Trp
            35                  40                  45

Asp Gln Gln Lys Gln Ala Gly Ile Asp Leu Leu Pro Val Gly Asp Phe
        50                  55                  60

Ala Trp Tyr Asp His Val Leu Thr Thr Ser Leu Leu Leu Gly Asn Val
65                  70                  75                  80

Pro Ala Arg His Gln Asn Lys Asp Gly Ser Val Asp Ile Asp Thr Leu
                85                  90                  95

Phe Arg Ile Gly Arg Gly Arg Ala Pro Thr Gly Glu Pro Ala Ala Ala
            100                 105                 110

Ala Glu Met Thr Lys Trp Phe Asn Thr Asn Tyr His Tyr Met Val Pro
            115                 120                 125

Glu Phe Val Lys Gly Gln Gln Phe Lys Leu Thr Trp Thr Lys Trp Thr
        130                 135                 140

Arg Arg Trp Arg Trp Ala Thr Arg
145                 150
```

RECOMBINANT MICROORGANISM FOR THE FERMENTATIVE PRODUCTION OF METHIONINE

RELATED APPLICATION DATA

This application is a National Stage Application under 35 U.S.C. 371 of co-pending PCT application PCT/IB2012/001336 designating the United States and filed Jun. 18, 2012 and is hereby incorporated herein by reference in its entirety for all purposes.

FIELD OF THE INVENTION

The present invention relates to a recombinant microorganism for the production of methionine and to a method for producing methionine, by culturing the recombinant microorganism in an appropriate culture medium comprising a source of carbon and a source of sulphur. The microorganism is modified in a way that the methionine/carbon source yield is increased by attenuating the activity of the cobalamin-independent methionine synthase. In particular, the gene metE is deleted in the recombinant microorganism.

PRIOR ART

Sulphur-containing compounds such as cysteine, homocysteine, methionine or S-adenosylmethionine are critical to cellular metabolism and are produced industrially to be used as food or feed additives and pharmaceuticals. In particular methionine, an essential amino acid, which cannot be synthesized by animals, plays an important role in many body functions. Aside from its role in protein biosynthesis, methionine is involved in transmethylation and in the bioavailability of selenium and zinc. Methionine is also directly used as a treatment for disorders like allergy and rheumatic fever. Nevertheless, most of the methionine that is produced is added to animal feed.

With the decreased use of animal-derived proteins as a result of BSE and chicken flu, the demand for pure methionine has increased. Commonly, D,L-methionine is produced chemically from acrolein, methyl mercaptan and hydrogen cyanide. However, the racemic mixture does not perform as well as pure L-methionine (Saunderson, 1985). Additionally, although pure L-methionine can be produced from racemic methionine, for example, through the acylase treatment of N-acetyl-D,L-methionine, this dramatically increases production costs. Accordingly, the increasing demand for pure L-methionine coupled with environmental concerns render microbial production of methionine an attractive prospect. Optimising the production of a chemical from a microorganism typically involves overexpressing proteins involved in the biosynthesis pathway, attenuating proteins involved in repression of the biosynthesis pathway or attenuating proteins involved in the production of undesirable by-products. All these approaches for the optimisation of L-methionine production in microorganisms have been described previously (see, for example, Patents or patent applications U.S. Pat. No. 7,790,424, U.S. Pat. No. 7,611,873, WO 2002/010209, WO 2005/059093 and WO 2006/008097); however, industrial production of L-methionine from microorganisms requires further improvements.

In *Escherichia coli* and in other microorganisms like *Corynebacterium glutamicum*, two distinct enzymes catalyze the terminal step in the de novo biosynthesis of methionine (Foster et al., 1961; Gonzalez et al., 1992). The cobalamin-dependent methionine synthase (MetH, EC 2.1.1.13) is encoded by the metH gene and contains a prosthetic group that is required for activity. The cobalamin-independent methionine synthase (MetE, EC 2.1.1.14) is encoded by the metE gene and has no known requirement for a vitamin-derived prosthetic group.

Numerous patents applications are related to the overproduction of MetH and MetE enzymes to enhance the last step of methionine biosynthesis, as for example:

WO2007/012078 and WO2007/135188 from BASF describe genetic alterations leading to overexpression of the genes metH and/or metE.

WO2009/144270 from EVONIK describes a method for producing methionine with a microorganism that displays an increased amount and/or activity of a cob(I)alamin-dependent MetH reactivation system.

Inventors have found, surprisingly and unexpectedly, that an attenuation of the amount and/or activity of the cobalamin-independent methionine synthase (MetE) leads to an improved production of methionine. This is the first time that the loss of activity of one of the enzymes belonging to the methionine biosynthesis pathway is proposed as being beneficial for the methionine production.

SUMMARY OF THE INVENTION

The invention relates to a recombinant microorganism optimised for the production of methionine, wherein the activity of the cobalamin-independent methionine synthase MetE is attenuated. Preferably, the gene metE encoding the MetE enzyme is deleted or mutated. The recombinant microorganism may also comprise other genetic modifications such as:

an increased expression of at least one of the following genes: ptsG, pyc, pntAB, cysP, cysU, cysW, cysA, cysM, cysJ, cysI, cysH, gcvT, gcvH, gcvP, lpd, serA, serB, serC, cysE, metF, metH, thrA, metA allele encoding for an enzyme with reduced feed-back sensitivity to S-adenosylmethionine and/or methionine (metA*), thrA, or a thrA allele encoding for an enzyme with reduced feed-back inhibition to threonine (thrA*) and/or an attenuated expression of one of the following genes: metJ, pykA, pykF, purU, ybdL or yncA.

In a particular embodiment, the present invention is related to a microorganism wherein: a) the gene metE is deleted, and b) the expression of the genes metA*, metH, cysPUWAM, cysJIH, gcvTHP, metF, serA, serB, serC, cysE, thrA* and pyc are enhanced; and c) the expression of the genes metJ, pykA, pykF, purU and yncA are attenuated.

The invention also relates to a method for the production of methionine or methionine derivatives in a fermentative process comprising the steps of: a) culturing the recombinant microorganism according to the invention in an appropriate culture medium comprising a fermentable source of carbon containing glucose and a source of sulphur and b) recovering methionine or methionine derivatives from the culture medium.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors that are reported in the publications and that might be used in connection with the invention. Nothing herein is to be construed as an admission that the invention is not entitled to antedate such disclosure by virtue of prior invention.

Furthermore, the practice of the present invention employs, unless otherwise indicated, conventional microbiological and molecular biological techniques within the skill of the art. Such techniques are well known to the skilled worker, and are explained fully in the literature. See, for example, Prescott et al. (1999) and Sambrook et al. (1989) (2001).

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

DEFINITIONS

The term "methionine" designates the essential sulphur-containing amino-acid with chemical formula $HO_2CCH(NH_2)CH_2CH_2SCH_3$ and CAS number 59-51-8 or 63-68-3 for the specific L-isomer.

"Derivatives of methionine" refers to molecules analogs to methionine which present the same chemical backbone but differ from methionine with at least one chemical group. In this invention, preferred methionine derivatives are N-acetyl methionine (NAM), S-adenosyl methionine (SAM) and hydroxy-methionine.

The term "microorganism", as used herein, refers to a bacterium, yeast or fungus which is not modified artificially. Preferentially, the microorganism is selected among Enterobacteriaceae, Bacillaceae, Streptomycetaceae and Corynebacteriaceae. More preferentially the microorganism is a species of *Escherichia*, *Klebsiella*, *Pantoea*, *Salmonella*, or *Corynebacterium*. Even more preferentially the microorganism is either the species *Escherichia coli* or *Corynebacterium glutamicum*.

The term "recombinant microorganism" or "genetically modified microorganism", as used herein, refers to a bacterium, yeast or fungus that is not found in nature and is genetically different from its equivalent found in nature. It means, it is modified either by introduction or by deletion or by modification of genetic elements. It can also be transformed by forcing the development and evolution of new metabolic pathways by combining directed mutagenesis and evolution under specific selection pressure (see, for example, WO 2004/076659).

A microorganism may be modified to express exogenous genes if these genes are introduced into the microorganism with all the elements allowing their expression in the host microorganism. The modification or "transformation" of microorganisms with exogenous DNA is a routine task for those skilled in the art.

A microorganism may be modified to modulate the expression level of an endogenous gene.

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product.

Another way to modulate their expression is to exchange the endogenous promoter of a gene (e.g., wild type promoter) with a stronger or weaker promoter to up or down regulate expression of the endogenous gene. These promoters may be homologous or heterologous. It is well within the ability of the person skilled in the art to select appropriate promoters.

The term "exogenous gene" means that the gene was introduced into a microorganism, by means well known by the man skilled in the art whereas this gene is not naturally occurring in the microorganism. Exogenous genes may be integrated into the host chromosome, or be expressed extra-chromosomally by plasmids or vectors. A variety of plasmids, which differ with respect to their origin of replication and their copy number in the cell, are well known in the art. These genes may be heterologous or homologous.

The term "heterologous gene" means that the gene is derived from a species of microorganism different from the recipient microorganism that expresses it. It refers to a gene which is not naturally occurring in the microorganism.

In the present application, all genes are referenced with their common names from *E. coli*. Their nucleotidic sequences are available on the websites http://www.ncbi.nlm.nih.gov/gene or http://www.ebi.ac.uk/embl/.

Using the references given in Genbank for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerate probes to clone the corresponding gene in another organism. These routine methods of molecular biology are well known to those skilled in the art, and are claimed, for example, in Sambrook et al, (1989) and (2001).

The terms "improved methionine production", "improve methionine production" and grammatical equivalents thereof, as used herein, refer to an increased methionine/ carbon source yield (ratio of gram/mol methionine produced per gram/mol carbon source consumed that it can be expressed in percent). Methods for determining the amount of carbon source consumed and of methionine produced are well known to those in the art. The yield is higher in the recombinant microorganism compared to the corresponding unmodified microorganism.

The terms "microorganism optimised for the fermentative production of methionine" refers to microorganisms evolved and/or genetically modified to present an improved methionine production in comparison with the endogenous production of the corresponding wild-type microorganisms. Such microorganisms "optimised" for methionine production are well known in the art, and have been disclosed in particular in patent applications WO2005/111202, WO2007/077041 and WO2009/043803.

According to the invention the terms "fermentative production", "culture" or "fermentation" are used to denote the growth of bacteria. This growth is generally conducted in fermenters with an appropriate culture medium adapted to the microorganism being used and containing at least one simple carbon source, and if necessary co-substrates.

An "appropriate culture medium" designates a medium (e.g., a sterile, liquid media) comprising nutrients essential or beneficial to the maintenance and/or growth of the cell such as carbon sources or carbon substrates, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "carbon source" or "carbon substrate" or "source of carbon" according to the present invention denotes any source of carbon that can be used by those skilled in the art to support the normal growth of a microorganism, including monosaccharides (such as glucose, galactose, xylose, fructose or lactose), oligosaccharides, disaccharides (such as sucrose, cellobiose or maltose), molasses, starch or its derivatives, hemicelluloses and combinations thereof. An especially preferred simple carbon source is glucose. Another preferred simple carbon source is sucrose. The carbon source can be derived from renewable feed-stock. Renewable feed-stock is defined as raw material required for certain industrial processes that can be regenerated within a brief delay and in sufficient amount to permit its transformation into the desired product. Vegetal biomass, treated or not, is an interesting renewable carbon source.

The term "source of sulphur" according to the invention refers to sulphate, thiosulfate, hydrogen sulphide, dithionate, dithionite, sulphite, methylmercaptan, dimethylsulfide and other methyl capped sulphides or a combination of the different sources. More preferentially, the sulphur source in the culture medium is sulphate or thiosulfate or a mixture thereof.

The terms "source of nitrogen" corresponds to either an ammonium salt or ammoniac gas. The nitrogen source is supplied in the form of ammonium or ammoniac.

The terms "attenuation" or "expression attenuated" mean in this context that the expression of a gene or an enzyme is decreased or suppressed compared to a non modified microorganism. Decrease or suppression of the expression of an enzyme is obtained by the attenuation of the expression of gene encoding said enzyme.

Attenuation of genes may be achieved by means and methods known to the man skilled in the art. Generally, attenuation of gene expression may be achieved by:
  Mutating the coding region or the promoter region or,
  Deleting of all or a part of the promoter region necessary for the gene expression or,
  Deleting the coding region of the gene by homologous recombination or
  Inserting an external element into coding region or into promoter region or
  Expressing the gene under control of a weak promoter.

The man skilled in the art knows a variety of promoters which exhibit different strength and which promoter to use for a weak genetic expression.

The term "activity" of an enzyme is used interchangeably with the term "function" and designates, in the context of the invention, the reaction that is catalyzed by the enzyme. The man skilled in the art knows how to measure the enzymatic activity of said enzyme. In particular, for measuring the activity of the protein MetE, see example 5.

The terms "attenuated activity" or "reduced activity" of an enzyme mean either a reduced specific catalytic activity of the protein obtained by mutation in the aminoacids sequence and/or decreased concentrations of the protein in the cell obtained by mutation of the nucleotidic sequence or by deletion of the coding region of the gene.

The terms "enhanced activity" or "increased activity" of an enzyme designates either an increased specific catalytic activity of the enzyme, and/or an increased quantity/availability of the enzyme in the cell, obtained for example by overexpressing the gene encoding the enzyme.

The terms "increased expression", "enhanced expression" or "overexpression" and grammatical equivalents thereof, are used interchangeably in the text and have a similar meaning. These terms mean that the expression of a gene or an enzyme is increased compared to a non modified microorganism. Increase expression of an enzyme is obtained by increasing expression of the gene encoding said enzyme.

To increase the expression of a gene, the man skilled in the art knows different techniques:
  Increasing the number of copies of the gene in the microorganism. The gene is encoded chromosomally or extrachromosomally. When the gene is located on the chromosome, several copies of the gene can be introduced on the chromosome by methods of recombination, known to the expert in the field (including gene replacement). When the gene is located extra-chromosomally, it may be carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (pSC101, RK2), low copy number plasmids (pACYC, pRSF1010) or high copy number plasmids (pSK bluescript II).
  Using a promoter inducing a high level of expression of the gene. The man skilled in the art knows which promoters are the most convenient, for example promoters Ptrc, Ptac, Plac, or the lambda promoter a are widely used. These promoters can be "inducible" by a particular compound or by specific external condition like temperature or light. These promoters may be homologous or heterologous.
  Attenuating the activity or the expression of a transcription repressor, specific or non-specific of the gene.

Using elements stabilizing the corresponding messenger RNA (Carrier and Keasling, 1998) or elements stabilizing the protein (e.g., GST tags, GE Healthcare).

The terms "encoding" or "coding" refer to the process by which a polynucleotide, through the mechanisms of transcription and translation, produces an amino-acid sequence. The gene(s) encoding the enzyme(s) can be exogenous or endogenous.

The terms "feed-back sensitivity" or "feed-back inhibition" refer to a cellular mechanism control in which an or several enzyme that catalyse the production of a particular substance in the cell are inhibited or less active when that substance has accumulated to a certain level. So the terms "reduced feed-back sensitivity" or "reduced feed-back inhibition" mean that the activity of such a mechanism is decreased or suppressed compared to a non modified microorganism. The man skilled in the art knows how to modify the enzyme to obtain this result. Such modifications have been described in the patent application WO 2005/111202 or in the U.S. Pat. No. 7,611,873.

The invention relates to a recombinant microorganism optimised for the fermentative production of methionine, wherein the activity of the cobalamin-independent methionine synthase MetE is attenuated.

The man skilled in the art knows many means and methods to attenuate enzymatic activity like protein mutation, gene mutation or attenuation of gene expression. Protein mutation may be achieved by replacing specific amino-acids present in the catalytic site of the enzyme, or introducing additional amino-acids, or deleting certain amino-acids.

In a first aspect of the invention, the expression of the metE gene, encoding the cobalamin-independent methionine synthase MetE, is attenuated. The nucleotide sequence of the *E. coli* metE gene is shown in SEQ ID NO 20.

Gene attenuation may be achieved by introducing foreign DNA into the gene to inactivate it or by expressing the gene under control of a weak promoter or an inducible promoter. The man skilled in the art knows a wide variety of promoters exhibiting different expression strength and/or different induction parameters and how to modify a promoter to decrease its expression strength by modifying the wild type promoter, for instance, in its consensus sequence, Ribosome Binding Site or start codon . . . . Thus, the man skilled in the art is able to chose a promoter which lead to an attenuate expression of metE.

In a preferred embodiment of the invention, at least a portion of the metE gene is deleted. Preferably this deleted portion represents at least 10% of the coding sequence, more preferably at least 20%, 30%, 40%, or 50% of the coding sequence. More preferably, at least 80% of the coding sequence is deleted. In a specific embodiment of the invention, the metE gene is completely deleted. The man skilled in the art knows many techniques to delete gene portions such as homologous recombination.

In a second aspect of the invention, the metE gene is mutated in order to encode a modified protein exhibiting attenuated activity. In a preferred embodiment of the invention, the mutation in the gene metE leads to the translation of a truncated MetE protein which is inactive. More preferably the mutation is a deletion of a portion of 13 base pairs (bp): from the $417^{th}$ to the $429^{th}$ base of the *E. coli* gene whose nucleotide sequence is shown in SEQ ID NO 20, leading to a frame shift mutation. Consequently, the translation of the protein is shortened (a stop codon is introduced by the frame shift) and gives rise to a truncated protein of 152 amino acids as shown in SEQ ID No 22) instead of 753 amino acids in the wild-type sequence, as shown in SEQ ID No 21. Any equivalent mutation allowing the introduction of a STOP codon in a metE gene from any microorganism species is also part of the invention.

Optimisation of Methionine Biosynthesis Pathway.

The recombinant microorganism according to the invention is modified for improving the production of methionine. Genes involved in methionine production are well known in the art, and comprise genes involved in the methionine specific biosynthesis pathway as well as genes involved in precursor-providing pathways and genes involved in methionine consuming pathways.

Efficient production of methionine requires the optimisation of the methionine specific pathway and several precursor-providing pathways. Methionine producing strains have already been described, in particular in patent applications WO2005/111202, WO2007/077041 and WO2009/043803. These applications are incorporated as reference into this application.

In a specific embodiment of the invention, the recombinant microorganism is modified as described below: the expression of at least one of the following genes is increased: ptsG, pyc, pntAB, cysP, cysU, cysW, cysA, cysM, cysJ, cysI, cysH, gcvT, gcvH, gcvP, lpd, serA, serB, serC, cysE, metF, metH, metA, thrA allele encoding for an enzyme with reduced feed-back sensitivity to S-adenosylmethionine and/or methionine (MetA*), thrA, and thrA allele encoding for an enzyme with reduced feed-back inhibition to threonine (thrA*).

ptsG encodes the PTS enzyme IICB$^{Glc}$ as described in patent application EP11305829.

pyc encodes a pyruvate carboxylase as described in patent application EP11305829. In a preferred embodiment, the pyc gene is heterologous and is chosen from pyc genes from *Rhizobium etli, Bacillus subtilis, Lactococcus lactis, Pseudomonas fluorescens* or *Corynebacterium* species, pntAB encode subunits of a membrane-bound transhydrogenase, such as described in patent application WO2012/055798, cysP encodes a periplasmic sulphate binding protein, as described in WO2007/077041 and in WO2009/043803, cysU encodes a component of sulphate ABC transporter, as described in WO2007/077041 and in WO2009/043803, cysW encodes a membrane bound sulphate transport protein, as described in WO2007/077041 and in WO2009/043803, cysA encodes a sulphate permease, as described in WO2007/077041 and in WO2009/043803, cysM encodes an O-acetyl serine sulfhydralase, as described in WO2007/077041 and in WO2009/043803, cysI and cysJ encode respectively the alpha and beta subunits of a sulfite reductase as described in WO2007/077041 and in WO2009/043803. Preferably cysI and cysJ are overexpressed together, cysH encodes an adenylylsulfate reductase, as described in WO2007/077041 and in WO2009/043803.

Increasing C1 metabolism is also a modification that leads to improved methionine production. It relates to the increase of the activity of at least one enzyme involved in the C1 metabolism chosen among GcvTHP, Lpd, MetF or MetH. In a preferred embodiment of the invention, the one carbon metabolism is increased by enhancing the expression and/or the activity of at least one of the following:

gcvT, gcvH, gcvP, and lpd, coding for the glycine cleavage complex, as described in patent application WO 2007/077041. The glycine-cleavage complex (GCV) is a multienzyme complex that catalyzes the oxidation of glycine, yielding carbon dioxide, ammonia, methylene-THF and a reduced pyridine nucleotide. The GCV complex consists of four protein components, the glycine dehydrogenase said P-protein (GcvP), the lipoyl-GcvH-protein said H-protein (GcvH), the aminomethyltransferase said T-protein (GcvT), and the dihydrolipoamide dehydrogenase said L-protein (GcvL or Lpd). P-protein catalyzes the pyridoxal phosphate-dependent liberation of CO2 from glycine, leaving a methylamine moiety. The methylamine moiety is transferred to the lipoic acid group of the H-protein, which is bound to the P-protein prior to decarboxylation of glycine. The T-protein catalyzes the release of NH3 from the methylamine group and transfers the remaining C1 unit to THF, forming methylene-THF. The L protein then oxidizes the lipoic acid component of the H-protein and transfers the electrons to NAD$^+$, forming NADH;

MetF encoding a methylenetetrahydrofolate reductase, as described in patent application WO 2007/077041;

MetH (B12-dependent homocysteine-N5-methyltrahydrofolate transmethylase) encoding methyltransferases.

The overexpression of at least one of the following genes involved in serine biosynthesis also reduces the production of the by-product isoleucine:

serA which encodes a phosphoglycerate dehydrogenase, as described in WO2007/077041 and in WO2009/043803, serB which encodes a phosphoserine phosphatase, as described in WO2007/077041 and in WO2009/043803, serC which encodes a phosphoserine aminotransferase, as described in WO2007/077041 and in WO2009/043803.

The overexpression of the following genes has already been shown to improve the production of methionine:

cysE encodes a serine acyltransferase; its overexpression allows an increase in methionine production, as described in WO 2007/077041;

metA encodes a homoserine succinyltransferase. The allele MetA* codes for an enzyme with reduced feed-back sensitivity to S-adenosylmethionine and/or methionine. Preferentially, the allele MetA* described in the patent application WO 2005/111202 is used;

thrA encodes an aspartokinase/homoserine dehydrogenase; the thrA* allele codes for an enzyme with reduced feed-back inhibition to threonine, as described in WO 2005/111202.

In a specific embodiment of the invention, genes may be under control of an inducible promoter. In a preferred embodiment of the invention, at least one of these genes is under the control of a temperature inducible promoter. Preferably, the expression of at least one of the genes: thrA, cysE, metA, is under the control of an inducible promoter, directly or indirectly. More preferably, the genes thrA, cysE and metA are under control of an inducible promoter, directly or indirectly. In a preferred embodiment of the invention, expression of thrA gene is under direct control of an inducible promoter and expression of cysE gene is under polar effect of inducible expression of thrA gene. In another preferred embodiment of the invention, expression of thrA gene is under direct control of an inducible promoter and expressions of cysE and metA genes are under polar effect of inducible expression of thrA gene.

In a most preferred embodiment, the temperature inducible promoter belongs to the family of $P_R$ promoters. A methionine producing strain having genes under control of inducible promoters is described in patent application WO2011/073122.

In another specific embodiment of the invention, the microorganism has been further modified, and the expression of at least one of the following genes is attenuated: metJ, pykA, pykF, purU, ybdL or yncA.

the gene metJ codes for the repressor protein MetJ (GenBank 1790373), responsible for the down-regulation of the methionine regulon as was suggested in patent application JP 2000/157267, The genes pykA and pykF code for the enzymes 'pyruvate kinase'. The attenuation of the expression of at least one or both of the pyruvate kinases decrease the consumption of phosphoenol pyruvate (PEP). Increased availability of PEP can increase the production of oxaloacetate, an important precursor of aspartate, which in turn is a precursor of methionine, as described in WO2007/077041 and in WO2009/043803, purU codes for a formyltetrahydrofolate deformylase, an enzyme that catalyzes the formyl-THF deformylase reaction. The attenuation of the deformylase activity increases the production of methyl-THF that is required for methylation of homocysteine. Loss of C1 metabolites by deformylation leads to an increased production of homocysteine that cannot be transformed into methionine. Homocysteine can then be a substrate for the enzyme cystathionine gamma synthase (MetB) that can catalyze the reaction between 0-succinylhomoserine and homocysteine resulting in the production of homolanthionine, as described in WO2007/077041 and in WO2009/043803, ybdL encodes an aminotransferase as described in patent application PCT/FR2010/052937, yncA encodes a N-acyltransferase, as described in patent application WO 2010/020681.

In a more preferred embodiment of the invention, the fermentative production of methionine by a recombinant microorganism, wherein the activity of the cob alamin-independent methionine synthase MetE is attenuated, from glucose as a main carbon source, may be achieved through a combination of the above discussed modifications in said microorganism, for example:

the expression of the gene metJ is attenuated and the expression of a metA allele encoding for an enzyme with reduced feed-back sensitivity to S-adenosylmethionine and/or methionine (MetA*) is enhanced;

the expression of the gene metJ is attenuated; the expression of a metA allele encoding for an enzyme with reduced feed-back sensitivity to S-adenosylmethionine and/or methionine (MetA*) is enhanced; and the expression of a thrA allele encoding for an enzyme with reduced feed-back inhibition to threonine (thrA*) is enhanced;

the expression of the gene metJ is attenuated; the expression of a metA allele encoding for an enzyme with reduced feed-back sensitivity to S-adenosylmethionine and/or methionine (MetA*) is enhanced; the expression of a thrA allele encoding for an enzyme with reduced feed-back inhibition to threonine (thrA*) is enhanced; and the expression of the gene cysE is enhanced;

the expression of the gene metJ is attenuated; the expression of a metA allele encoding for an enzyme with reduced feed-back sensitivity to S-adenosylmethionine and/or methionine (MetA*) is enhanced; the expression of a thrA allele encoding for an enzyme with reduced feed-back inhibition to threonine (thrA*) is enhanced;

the expression of the gene cysE is enhanced; and the expression of the genes metF and/or metH is enhanced.

In a particular aspect of the invention, the recombinant microorganism comprises the following genetic modifications:

the gene metE is deleted,
the expression of the genes metA*, metH, cysPUWAM, cysJIH, gcvTHP, metF, serA, serB, serC, cysE, thrA* and pyc are enhanced, and
the genes metJ, pykA, pykF, purU and yncA are attenuated.

In a particular embodiment of the invention, the microorganism is from the bacterial family Enterobacteriaceae or Corynebacteriaceae.

Preferentially, the microorganism is *Escherichia coli* or *Corynebacterium glutamicum*.

Culture Conditions

The invention is also related to a method of production of methionine comprising the followings steps:

Culturing a recombinant microorganism in an appropriate culture medium comprising a fermentable source of carbon and a source of sulphur, and,
Recovering methionine or its derivatives from the culture medium.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

For *E. coli*, the culture medium can be of identical or similar composition to an M9 medium (Anderson, 1946), an M63 medium (Miller, 1992); or a medium such as defined by Schaefer et al., (1999).

For *C. glutamicum*, the culture medium can be of identical or similar composition to BMCG medium (Liebl et al., 1989) or to a medium such as described by Riedel et al., (2001).

In some embodiment of the invention, the culture is subjected to a limitation or starvation for one or several inorganic substrate. It refers to condition under which growth of the microorganisms is governed by the quantity of an inorganic chemical supplied that still permits weak growth. Such limitation in microorganism growth has been described in the patent application WO 2009/043372. In a preferred embodiment of the invention, the culture is subjected to phosphate limitation.

The action of "recovering methionine or its derivatives from the culture medium" designates the action of recovering L-methionine and/or one of its derivatives, in particular N-acetyl methionine (NAM) and S-adenosyl methionine (SAM) and all other derivatives that may be useful. The methods for the recovery and purification of the produced compounds are well known to those skilled in the art (see in particular WO 2005/007862, WO 2005/059155).

The amount of product in the fermentation medium can be determined using a number of methods known in the art, for example, high performance liquid chromatography (HPLC) or gas chromatography (GC). For example the quantity of methionine obtained in the medium is measured by HPLC after OPA/Fmoc derivatization using L-methionine (Fluka, Ref 64319) as a standard. The amount of NAM is determinated using refractometric HPLC using NAM (Sigma, Ref 01310) as a standard.

EXAMPLES

The present invention is further defined in the following examples. It should be understood that these examples, while indicating preferred embodiments of the invention, are given by way of illustration only. From above disclosure and these examples, the man skilled in the art can make various changes of the invention to adapt it to various uses and conditions without modify the essentials means of the invention.

In particular, examples show modified *Escherichia coli* (*E. coli*) strains, but these modifications can easily be performed in other microorganisms of the same family.

*Escherichia coli* belongs to the Enterobacteriaceae family, which comprises members that are Gram-negative, rod-shaped, non-spore forming and are typically 1-5 µm in length. Most members have flagella used to move about, but a few genera are non-motile. Many members of this family are a normal part of the gut flora found in the intestines of humans and other animals, while others are found in water or soil, or are parasites on a variety of different animals and plants. *E. coli* is one of the most important model organisms, but other important members of the Enterobacteriaceae family include *Klebsiella*, in particular *Klebsiella terrigena*, *Klebsiella planticola* or *Klebsiella oxytoca*, and *Salmonella*.

Moreover, several patent applications point out that optimisation for methionine production can easily be applied in *E. coli* and in *Corynebacterium glutamicum* without undue experimentation.

Example 1

Protocoles

Several protocols have been used to construct methionine producing strains described in the following examples.

Protocol 1:

Chromosomal Modifications by Homologous Recombination and Selection of Recombinants (Datsenko, & Wanner, (2000)).

Allelic replacement or gene insertion in specified chromosomal locus was carried out by homologous recombination as described by Datsenko & Wanner (2000). The kanamycin (Km) resistance kan, flanked by Flp recognition sites was amplified by PCR by using pKD4 plasmid as template. The resulting PCR products were used to transform the recipient *E. coli* strain harbouring plasmid pKD46 that expresses the λ Red (γ, β, exo) recombinase. Antibiotic-resistant transformants were then selected and the chromosomal structure of the modified locus was verified by PCR analysis with the appropriate primers listed in Table 3.

The kan resistance gene can be excised by using plasmid pCP20 that carries the gene coding Flp recombinase as described by Datsenko & Wanner (2000). The pCP20 plasmid was introduced into the appropriated strain and the transformants were spread on LB supplemented with ampicillin at 30° C. In order to express the flp gene and to remove the kanamycin cassette, the transformants were cultivated at 37° C. Then after isolation, the antibiotic sensible clones were verified by PCR using oligonucleotides listed in Table 3.

Protocol 2:

Transduction of Phage P1

Chromosomal modifications were transferred to a given *E. coli* recipient strain by P1 transduction. The protocol includes 2 steps: (i) preparation of the phage lysate on a donor strain containing the resistance associated chromosomal modification and (ii) infection of the recipient strain by this phage lysate.

Preparation of the Phage Lysate

Inoculate 100 μl of an overnight culture of the strain MG1655 with the chromosomal modification of interest in 10 ml of Km 50 μg/ml+glucose 0.2%+CaCl$_2$ 5 mM.

Incubate 30 min at 37° C. with shaking.

Add 100 μl of P1 phage lysate prepared on the donor strain MG1655 (approx. 1×10$^9$ phage/ml).

Shake at 37° C. for 3 hours until the complete lysis of the cells.

Add 200 μl of chloroform, and vortex

Centrifuge 10 min at 4500 g to eliminate cell debris.

Transfer of supernatant to a sterile tube.

Store the lysate at 4° C.

Transduction

Centrifuge 10 min at 1500 g 5 ml of an overnight culture of the E. coli recipient strain cultivated in LB medium.

Suspend the cell pellet in 2.5 ml of MgSO$_4$ 10 mM, CaCl$_2$ 5 mM.

Infect 100 μl cells with 100 μl P1 phage of strain MG1655 with the modification on the chromosome (test tube) and as a control tubes 100 μl cells without P1 phage and 100 μl P1 phage without cells.

Incubate 30 min at 30° C. without shaking.

Add 100 μl sodium citrate 1 M in each tube, and vortex.

Add 1 ml of LB.

Incubate 1 hour at 37° C. with shaking

Centrifuge 3 min at 7000 rpm.

Plate on LB+Km 50 μg/ml

Incubate at 37° C. overnight.

TABLE 1

Strains (number and genotype) cited or described in the following examples.

| Strain number | Genotype |
|---|---|
| 1 | MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC |
| 2 | MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-met4*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07::Km |
| 3 | MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07 |
| 4 | MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM::RN/PR01/RBS01-thr4*1-cysE-PgapA-metA*11 ΔtreBC::RN/serA-serC ΔyjbI-RN/Ptrc01/RBS01-gcvTHP-TT07::Km (pCL1920-PgapA-pycre-TT07) |
| 5 | MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01 -thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM:RN/PR01/RBS01-thrA*1-cysE-PgapA-metA*11 ΔtreBC::RN/serA-serC ΔyjbI::RN/Ptrc01/RBS01-gcvTHP-TT07::Km (pCL1920-PgapA-pycre-TT07) (pCC1BAC-TT02-Ptrc30/RBS01-serC-TT07*2-Ptrc30/RBS01-serA-TTadcca) |
| 6 | MG1655 metA*11 metE::Km Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM:RN/PR01/RBS01-thrA*1-cysE-PgapA-metA*11 ΔtreBC::RN/serA-serC ΔyjbI::RN/Ptrc01/RBS01-gcvTHP-TT07 |
| 7 | MG1655 metA*11 metE::Km Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM:RN/PR01/RBS01-thrA*1-cysE-PgapA-metA*11 ΔtreBC::RN/serA-serC ΔyjbI::RN/Ptrc01/RBS01-gcvTHP-TT07 (pCL1920-PgapA-pycre-TT07) (pCC1BAC-TT02-Ptrc30/RBS01-serC-TT07*2-Ptrc30/RBS01-serA-TTadcca) |

TABLE 2

Correspondence between the previous and the current nomenclature for the genotype of strain 1 described in patent application EP10306164.

| Previous nomenclature | Current nomenclature |
| --- | --- |
| MG1655 metA*11 | MG1655 metA*11 |
| Ptrc-metH | Ptrc01*2/RBS08*1-metH |
| PtrcF-cysPUWAM | Ptrc01-cysPUWAM |
| PtrcF-cysJIH | Ptrc01-cysJIH |
| Ptrc09-gcvTHP | Ptrc01/RBS01-gcvTHP |
| Ptrc36-ARNmst17-metF | Ptrc01/ARN01/RBS01-metF |
| Ptrc01-serB | Ptrc94-serB |
| ΔmetJ ΔpykF ΔpykA ΔpurU ΔyncA | ΔmetJ ΔpykF ΔpykA ΔpurU ΔyncA |
| ΔmalS::TTadc-CI857-PlambdaR*(−35)-thrA*1-cysE | ΔmalS::RN/PRM-CI857-TTadcca-PR01/RBS01*4-thrA*1-cysE |
| ΔPgaABCD::TT02-TTadc-PlambdaR*(−35)-RBS01-thrA*1-cysE-PgapA-metA*11 | ΔPgaABCD::RN/PR01/RBS01-thrA*1-cysE-PgapA-metA*11 |
| ΔuxaCA::TT07-TTadc-PlambdaR*(−35)-RBS01-thrA*1-cysE-PgapA-metA*11 | ΔuxaCA::RN/PR01/RBS01-thrA*1-cysE-PgapA-metA*11 |
| ΔCP4-6::TT02-TTadc-PlambdaR*(−35)-RBS01-thrA*1-cysE-PgapA-metA*11 | ΔCP4-6::RN/PR01/RBS01-thrA*1-cysE-PgapA-metA*11 |
| ΔwcaM::TT02-TTadc-PlambdaR*(−35)-RBS01-thrA*1-cysE-PgapA-metA*11 | ΔwcaM::RN/PR01/RBS01-thrA*1-cysE-PgapA-metA*11 |
| ΔtreBC::TT02-serA-serC | ΔtreBC::RN/serA-serC |

TABLE 3

Oligonucleotides used in the following examples.

| Oligonucleotide name | SEQ ID N° | Sequence 5' → 3' |
| --- | --- | --- |
| YjbIup-F | 1 | cgtaggcgccggtaccgagtgcagatcggctggaaggcg |
| YjbIup-R | 2 | gcttgtatacaacagataaaacgaaaggcccagtctttcgactgagcctttcgttttat ttgatgcatttctgtagaattttacacttatagtatcattactgattgagacttca |
| YjbIdown-F | 3 | agactgggcctttcgttttatctgttgtatacaagctttacctagggcccttaattaaata atgaataagggtgtttaagtaaaggaaaacatcaccgttcctggcat |
| YjbIdown-R | 4 | cgtaggcgccggtacccagcataatcattcaccacacatccg |
| Km-F | 5 | tcccccggggtataccatatgaatatcctccttag |
| Km-R | 6 | gcccaagctttgtaggctggagctgcttcg |
| Ptrc01/RBS01-GcvTHP-F | 7 | cgtaggcctgggcccgagctgttgacaattaatcatccg |
| GcvTHP-TT07-R | 8 | cgaaggcctttaattaagcagaaaggcccacccgaaggtgagccaggcggccg cttactggtattcgctaatcggtacg |
| yjbI-gcvTHP-F | 9 | cagaccacccaactggcgacc |
| yjbI-gcvTHP-R | 10 | gccattggaatcgaccagcc |
| Ptrc30/RBS01-F | 11 | tcggcgccttaattaacatcaaataaaacgaaaggctcagtcgaaagactgggcct ttcgtttatctgtttacgtagagctgttgacgattaatcatccggctcgtatactgtgtg gaataaggaggtatatt |
| Ptrc30/RBS01-serC-R | 12 | ccagaactaaaattgaagatttgagccataatatacctccttattccacacagtat acgagc |
| serC-TT07*2-R | 13 | cccaagcttgcatgcgctagcgagctcgagaaaggcccacccgaaggtgagcca ggttaaccgtgacggcgttcg |
| Ptrc30/RBS01-serA-F | 14 | tacgtagctagcgagctgttgacgattaatcatccggctcgtatactgtgtggaataa ggaggtatattatggcaaaggtatcgctggagaaag |
| serA-TTadcca-R | 15 | cccaagcttgcatgccctaggtaaaaaaaataagagttaccatttaaggtaactctta tttttattagtacagcagacgggcgcg |
| metE-Km-F | 16 | agaaaccgcgcggcactggcgaacatggtgcaggcggcgcagaacttgcgtc gggggtaaaatccaaaccgggtggtaataccacccggtcttttctcatgtaggctg gagctgcttcg |

TABLE 3-continued

Oligonucleotides used in the following examples.

| Oligonucleotide name | SEQ ID N° | Sequence 5' → 3' |
|---|---|---|
| metE-Km-R | 17 | gcagaagatggctggcagcgtatgctggaatggtttaagcagtatggtgggaaga agtcgctgtaagcagaaaggcccacccgaaggtgagccagtgtgacatatgaata tcctccttag |
| metE-F | 18 | cgtttgggactggatgtgctgg |
| metE-R | 19 | gcgtggtacggcaaactgac |

Example 2

Construction of Strain 5, MG1655 metA*11 Ptrc01*2/RBS08*1-metH Ptrc01-cysPUWAM Ptrc01-cysJIH Ptrc01/RBS01-gcvTHP Ptrc01/ ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD:: RN/PR01/RBS01-thrA*1-cysE-PgapA-metA*1 1 ΔuxaCA::RN/PR01/RBS01-thrA*1-cysE-PgapA-metA*1 1 ΔCP4-6::RN/PR01/RBS01-thrA*1-cysE-PgapA-metA*1 1 ΔwcaM::RN/PR01/RBS01-thrA*1-cysE-PgapA-metA*1 1 ΔtreBC::RN/serA-serC ΔyjbI::RN/Ptrc01/RBS01-gcvTHP-TT07::Km (pCL1920-PgapA-pycre-TT07) (pCC1BAC-TT02-Ptrc30/RBS01-serC-TT07*2-Ptrc30/RBS01-serA-TTadcca)

1. Strain 1

The methionine producing strain 1 (genotype in table 1) has been described in patent application EP10306164 which is incorporated as reference into this application.

2. Construction of the Strain 2

To increase the methylene-tetrahydrofolate pool into the cell, the glycine cleavage complex encoded by gcvTHP operon was overproduced by adding one copy of this operon on the chromosome at the yjbI locus. This additional copy of gcvTHP was expressed using an artificial inducible trc promoter and an optimised ribosome binding site, giving the ΔyjbI::RN/Ptrc01/RBS01-gcvTHP-TT07::Km chromosomal integration.

To delete the yjbI gene and replace it by the Ptrc01/RBS01-gcvTHP-TT07 region, the homologous recombination strategy described by Datsenko & Wanner (2000) was used. This strategy allows the insertion of a chloramphenicol or a kanamycin resistance cassette but also an additional DNA, while deleting most of the genes concerned. For this purpose, the following plasmid was constructed, pUC18-ΔyjbI::TT02-Ptrc01/RBS01-gcvTHP-TT07::Km.

This pUC18-ΔyjbI::TT02-Ptrc01/RBS01-gcvTHP-TT07::Km plasmid is derived from the pUC18 vector (Norrander et al., 1983) and harbors the kanamycin resistance cassette associated to Ptrc01/RBS01-gcvTHP-TT07 region, both cloned between the upstream and the downstream regions of yjbI.

For the construction of pUC18-ΔyjbI::TT02-Ptrc01/RBS01-gcvTHP-TT07::Km, first the pUC18-ΔyjbI::TT02-SMC plasmid was constructed. This plasmid carries the upstream and the downstream regions of yjbI which are separated by a transcriptional terminator (T$_1$ of rrnB gene of E. coli, named TT02) and a multiple cloning site (composed of BstZ17I, HindIII, AvrII, ApaI and PacI restriction sites, named SMC). This last region was PCR amplified from genomic DNA using the following oligonucleotides:

YjbIup-F (SEQ ID NO 1)

CGTAGGCGCCGGTACCgagtgcagatcggctggaaggcg with
a region (lower case) homologous to the sequence (4247987-4248009) of the yjbI region (reference sequence on the website http://www.ecogene.org/),
a region (upper case) for SfoI and KpnI restriction site and extra-bases.

YjbIup-R (SEQ ID NO 2)

GCTTGTATACAACAGATAAAACGAAAGGCCCAGTCTTTCGACTGAGCCTT

TCGTTTTATTTGATGcatttctgtagaattttacacttatagtatcatta ctgattgagacttca with
a region (lower case) homologous to the sequence (4248931-4248980) of the yjbI region (reference sequence on the website http://www.ecogene.org/),
a region (upper bold case) for transcription terminator T$_1$ of rrnB gene of E. coli (Orosz et al, 1991),
a region (upper case) for BstZ17I restriction site and part of the HindIII restriction site of the multiple cloning site.

YjbIdown-F (SEQ ID NO 3)

AGACTGGGCCTTTCGTTTTATCTGTTGTATACAAGCTTTACCTAGGGCCC

TTAATTAAataatgaataagggtgtttaagtaaaggaaaacatcaccgtt cctggcat with
a region (lower case) homologous to the sequence (4250286-4250335) of the yjbI region (reference sequence on the website http://www.ecogene.org/),
a region (upper bold case) for part of the transcription terminator T$_1$ of rrnB gene of E. coli (Orosz et al., 1991),
a region (upper case) for the entire multiple cloning site.

YjbIdown-R (SEQ ID NO 4)

CGTAGGCGCCGGTACCcagcataatcattcaccacacatccg with
a region (lower case) homologous to the sequence (4251224-4251249) of the yjbI region (reference sequence on the website http://www.ecogene.org/), a region (upper case) for SfoI and KpnI restriction site and extra-bases.

First, the "upYjbI" and "downYjbI" fragments were PCR amplified from MG1655 genomic DNA using YjbIup-F/YjbIup-R and YjbIdown-F/YjbIdown-R oligonucleotides, respectively. Secondly, "upYjbI-downYjbI" fragment was amplified from "upYjbI" and "downYjbI" PCR fragments (that possess an overlapping region including a part of the transcription terminator $T_1$ of rrnB gene of *E. coli* and a part of the multiple cloning site) using YjbIup-F/YjbIdown-R oligonucleotides. The "upYjbI-downYjbI" PCR fragment was cut with the restriction enzyme SfoI and cloned into the blunted EcoRI/HindIII sites of the pUC18 vector, giving the pUC18-ΔyjbI::TT02-SMC plasmid.

Then, the kanamycin resistance cassette was PCR amplified from pKD4 vector using the following oligonucleotides:
Km-F (SEQ ID NO 5)

TCCCCCGGGGTATACcatatgaatatcctccttag with
a region (lower case) for the amplification of the kanamycin resistance cassette (reference sequence in Datsenko & Wanner, 2000,
a region (upper case) for SmaI and BstZ17I restriction sites and extra-bases.
Km-R (SEQ ID NO 6)

GCCCAAGCTTtgtaggctggagctgcttcg with
a region (lower case) for the amplification of the kanamycin resistance cassette (reference sequence in Datsenko & Wanner, 2000
a region (upper case) for HindIII restriction site and extra-bases.

The PCR fragment was cut with the restriction enzymes BstZ17I and HindIII and cloned into the BstZ17I/HindIII sites of the pUC18-ΔyjbI::TT02-SMC plasmid, giving the pUC18-ΔyjbI::TT02-SMC::Km plasmid.

Finally, the Ptrc01/RBS01-gcvTHP-TT07 fragment was PCR amplified from the genomic DNA of strain 1 using Ptrc01/RBS01-GcvTHP-F/GcvTHP-TT07-R oligonucleotides (described below). The PCR fragment was cut with the restriction enzymes ApaI and PacI and cloned into the ApaI/PacI sites of the pUC18-ΔyjbI::TT07-SMC::Km plasmid, giving the pUC18-ΔyjbI::TT02-Ptrc01/RBS01-gcvTHP-TT07::Km plasmid.

Recombinant plasmids were verified by DNA sequencing.
Ptrc01/RBS01-GcvTHP-F (SEQ ID NO 7)

CGTAGGCCTGGGCCCgagctgttgacaattaatcatccg with
a region (lower case) homologous to a part of the artificial inducible trc promoter located upstream of gcvTHP operon in the strain 1,
a region (upper case) for StuI and ApaI restriction sites and extra-bases.
GcvTHP-TT07-R (SEQ ID NO 8)

CGAAGGCCTTTAATTAAGCAGAAAGGCCCACCCGAAGGTGAGCCAGGCGG
CCGCttactggtattcgctaatcggtacg with
a region (lower case) homologous to the sequence (3044190-3044214) of the gcvP gene (reference sequence on the website http://www.ecogene.org/),
a region (upper bold case) for T7te transcriptional terminator sequence, named TT07 (Harrington et al., 2001),
a region for PacI, StuI restriction sites and extra-bases.

Finally, the ΔyjbI::TT02-Ptrc01/RBS01-gcvTHP-TT07::Km fragment was obtained by cutting the pUC18-ΔyjbI::TT02-Ptrc01/RBS01-gcvTHP-TT07::Km plasmid with KpnI restriction enzyme and was then introduced by electroporation, according Protocol 1, into a MG1655 metA*11 pKD46 strain. The kanamycin resistant transformants were then selected, and the insertion of the ΔyjbI::TT02-Ptrc01/RBS01-gcvTHP-TT07::Km fragment was verified by a PCR analysis with the oligonucleotides yjbI-gcvTHP-F and yjbI-gcvTHP-R. The verified and selected strain was called MG1655 metA*11 pKD46 ΔyjbI::RN/Ptrc01/RBS01-gcvTHP-TT07::Km.
yjbI-gcvTHP-F (SEQ ID NO 9)

cagaccacccaactggcgacc homologous to the sequence (4247754-4247774) of yjbI region (reference sequence on the website http://www.ecogene.org/)
yjbI-gcvTHP-R (SEQ ID NO 10)

gccattggaatcgaccagcc homologous to the sequence (4251489-4251508) of the yjbI region (reference sequence on the website http://www.ecogene.org/)

The ΔyjbI::RN/Ptrc01/RBS01-gcvTHP-TT07::Km chromosomal modification was then transduced into the strain 1, according to Protocol 2.

Kanamycin resistant transductants were selected and the presence of ΔyjbI::RN/Ptrc01/RBS01-gcvTHP-TT07::Km chromosomal modification was verified by PCR with primers yjbI-gcvTHP-F and yjbI-gcvTHP-R.

The resulting strain MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-C1857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07::Km was named strain 2.

3. Construction of the Strain 3

For construction of strain 3, the resistance cassette associated to the chromosomal integration ΔyjbI::RN/Ptrc01/RBS01-gcvTHP-TT07::Km of strain 2 was removed according to Protocol 1.

Kanamycin sensible clones were selected and the absence of the kanamycin cassette was verified by PCR with primers yjbI-gcvTHP-F and yjbI-gcvTHP-R.

The resulting strain MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-C1857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapAmetA*11 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07 was named strain 3.

4. Construction of the Strain 4

The plasmid pCL1920-PgapA-pycre-TT07, described in patent application PCT/FR2010/052937 (which is incorporated as reference into this application), was introduced into strain 2, giving the following strain MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07::Km (pCL1920-PgapA-pycre-TT07), named strain 4.

5. Construction of the Strain 5

To increase the flux into the serine pathway, the serC and serA genes were overexpressed owing artificial promoters and an optimised ribosome binding sites and using of the bacterial artificial chromosome pCC1BAC (Epicentre). For this purpose, the following plasmid pCC1BAC-TT02-Ptrc30/RBS01-serC-TT07*2-Ptrc30/RBS01-serA-TTadcca was constructed.

For the construction of pCC1BAC-TT02-Ptrc30/RBS01-serC-TT07*2-Ptrc30/RBS01-serA-TTadcca, the "TT02-Ptrc30/RBS01-serC-TT07*2" and "Ptrc30/RBS01-serA-TTadcca" regions were PCR amplified.

For the "TT02-Ptrc30/RBS01-serC-TT07*2" region, at first a megaprimer harbouring the transcriptional terminator ($T_1$ of rrnB, annotated TT02), the artificial promoter (Ptrc30), the optimised ribosome binding site (RBS01) and the beginning of serC gene was synthesized by a short PCR using the oligonucleotides Ptrc30/RBS01-F and Ptrc30/RBS01-serC-R (described below) without adding matrix. Secondly, the "TT02-Ptrc30/RBS01-serC-TT07*2" fragment was amplified by PCR using E. coli MG1655 genomic DNA as matrix and the synthesized megaprimer and the serC-TT07*2-R oligonucleotide (described below).

Ptrc30/RBS01-F (SEQ ID NO 11)

tcggcgccttaattaaCATCAAATAAAACGAAAGGCTCAGTCGAAAGACT

GGGCCTTTCGTTTTATCTGTTtacgtaGAGCTGTTGACGATTAATCATCC

GGCTCGTATACTGTGTGGAA*TAAGGAGGTATATT* with
- a region (upper bold case) for transcription terminator $T_1$ of rrnB gene of E. coli (Orosz et al., 1991),
- a region (upper underlined case) homologous to the artificial inducible trc promoter,
- a region (upper italic case) homologous to an optimised ribosome binding site,
- a region (lower case) for NarI, PacI restriction sites and extra-bases.

Ptrc30/RBS01-serC-R (SEQ ID NO 12)

ccagaactaaaattgaagatttgagccat*AATATACCTCCTTATTCCACA*

CAGTATACGAGC with
- a region (upper underlined case) homologous to the artificial inducible trc promoter,
- a region (upper italic case) homologous to an optimised ribosome binding site,
- a region (lower case) homologous to the sequence (956876-956904) of serC gene (reference sequence on the website http://www.ecogene.org/).

serC-TT07*2-R (SEQ ID NO 13)

CCCAAGCTTGCATGCGCTAGCGAGCTCGAGAAAGGCCCACCCGAAGGTGA

GCCAGGttaaccgtgacggcgttcg with
- a region (upper bold case) for T7te transcriptional terminator sequence (Harrington et al., 2001) which possesses a base deletion at the $29^{th}$ position (named TT07*2),
- a region (lower case) homologous to the sequence (957946-957964) of serC gene (reference sequence on the website http://www.ecogene.org/),
- a region (upper case) for HindIII, SphI, SacI and NheI restriction sites and extra-bases.

In the same manner, the "Ptrc30/RBS01-serA-TTadcca" fragment was amplify by PCR using E. coli MG1655 genomic DNA as matrix and the Ptrc30/RBS01-serA-F and serA-TTadcca-R oligonucleotides (described below).

Ptrc30/RBS01-serA-F (SEQ ID NO 14)

TACGTAGCTAGCGAGCTGTTGACGATTAATCATCCGGCTCGTATACTGTG

TGGAA*TAAGGAGGTATATT*atggcaaaggtatcgctggagaaag with
- a region (upper underlined case) homologous to the artificial inducible trc promoter,
- a region (upper italic case) homologous to an optimised ribosome binding site,
- a region (lower case) homologous to the sequence (3056408-3056432) of serA gene (reference sequence on the website ht http://www.ecogene.org/),
- a region (upper case) for NheI restriction site and extra-bases.

serA-TTadcca-R (SEQ ID NO 15)

CCCAAGCTTGCATGCCCTAGGTAAAAAAAATAAGAGTTACCATTTAAGGT

AACTCTTATTTTTAttagtacagcagacgggcgcg

- a region (upper bold case) for TTadc transcriptional terminator sequence (transcription terminator of the adc gene from Clostridium acetobutylicum, homologous from 179847 to 179807 of the pSLO1 megaplasmid),
- a region (lower case) homologous to the sequence (3055200-3055220) of serA gene (reference sequence on the website http://www.ecogene.org/),
- a region (upper case) for AvrII, SphI, HindIII restriction sites and extra-bases.

The PCR fragments, "TT02-Ptrc30/RBS01-serC-TT07*2" and the "Ptrc30/RBS01-serA-TTadcca" were cut with the restriction enzymes NarI/NheI, and NheI/SphI, respectively, and both cloned into the NarI/SphI sites of the pCC1BAC plasmid, giving the pCC1BAC-TT02-Ptrc30/RBS01-serC-TT07*2-Ptrc30/RBS01-serA-TTadcca plasmid.

The recombinant plasmid was verified by DNA sequencing.

Finally, the plasmid pCC1BAC-TT02-Ptrc30/RBS01-serC-TT07*2-Ptrc30/RBS01-serA-TTadcca was introduced into strain 4, giving the following strain MG1655 metA*11 Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07::Km (pCL1920-PgapA-pycre-TT07) (pCC1BAC-TT02-Ptrc30/RBS01-serC-TT07*2-Ptrc30/RBS01-serA-TTadcca), named strain 5.

6. Identification of the MetE Mutation in Strain 5

By measuring the methionine synthase activity (METE) of the strain 5, we identified that the metE gene was not functional, because of some mutations giving a truncated MetE protein.

The mutation is a deletion of 13 bp (the 417$^{th}$ to the 429$^{th}$ base of the gene) of the metE gene leading to a frame shift mutation. Consequently, the translation of the protein is shortened (stop codon introduced by the frame shift) and gives rise to a truncated protein of 152 amino acids instead of 753.

Here is the Sequence of the WT MetE Protein (SEQ ID NO 21):

MTILNHTLGFPRVGLRRELKKAQESYWAGNSTREELLAVGRELRARHWDQ

QKQAGIDLLPVGDFAWYDHVLTTSLLLGNVPARHQNKDGSVDIDTLFRIG

RGRAPTGEPAAAAEMTKWFNTNYHYMVPEFVKGQQFKLTWTQLLDEVDEA

LALGHKVKPVLLGPVTWLWLGKVKGEQFDRLSLLNDILPVYQQVLAELAK

RGIEWVQIDEPALVLELPQAWLDAYKPAYDALQGQVKLLLTTYFEGVTPN

LDTITALPVQGLHVDLVHGKDDVAELHKRLPSDWLLSAGLINGRNVWRAD

LTEKYAQIKDIVGKRDLWVASSCSLLHSPIDLSVETRLDAEVKSWFAFAL

QKCHELALLRDALNSGDTAALAEWSAPIQARRHSTRVHNPAVEKRLAAIT

AQDSQRANVYEVRAEAQRARFKLPAWPTTTIGSFPQTTEIRTLRLDFKKG

NLDANNYRTGIAEHIKQAIVEQERLGLDVLVHGEAERNDMVEYFGEHLDG

FVFTQNGWVQSYGSRCVKPPIVIGDISRPAPITVEWAKYAQSLTDKPVKG

MLTGPVTILCWSFPREDVSRETIAKQIALALRDEVADLEAAGIGIIQIDE

PALREGLPLRRSDWDAYLQWGVEAFRINAAVAKDDTQIHTHMCYCEFNDI

MDSIAALDADVITIETSRSDMELLESFEEFDYPNEIGPGVYDIHSPNVPS

VEWIEALLKKAAKRIPAERLWVNPDCGLKTRGWPETRAALANMVQAAQNL

RRG*

Here is the Sequence of the Truncated MetE* Protein (SEQ ID NO 22):

MTILNHTLGFPRVGLRRELKKAQESYWAGNSTREELLAVGRELRARHWDQ

QKQAGIDLLPVGDFAWYDHVLTTSLLLGNVPARHQNKDGSVDIDTLFRIG

RGRAPTGEPAAAAEMTKWFNTNYHYMVPEFVKGQQFKLTWTKWTRRWRWA

TR*

Example 3

Construction of Strain 7, MG1655 metA*11 metE::Km Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA* 1 1 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07 (pCL1920-PgapA-pycre-TT07) (pCC1BAC-TT02-Ptrc30/RBS01-serC-TT07*2-Ptrc30/RBS01-serA-TTadcca)

1. Construction of the Strain 6

To study if restoration of a functional MetE protein could modify the methionine production of the strain 5, we replaced the truncated metE gene by a wild-type one using the homologous recombination strategy described by Datsenko & Wanner (2000).

For this purpose, the kanamycin cassette flanked with fragments homologous to the metE region, "metE::Km" fragment was PCR amplified using oligonucleotides metE-Km-F and metE-Km-R (described below). The "metE::Km" fragment was introduced into a MG1655 metA*11 pKD46 strain which possesses a functional version of the metE gene.

metE-Km-F (SEQ ID NO 16)

agaaacccgcgcggcactggcgaacatggtgcaggcggcgcagaacttgc gtcgggggtaaaatccaaaccgggtggtaataccacccggtcttttctca

TGTAGGCTGGAGCTGCTTCG with

- a region (lower case) homologous to the sequence (4013277-4013376) of metE region (reference sequence on the website http://www.ecogene.org/),
- a region (upper case) for the amplification of the kanamycin resistance cassette (reference sequence in Datsenko & Wanner, 2000.

metE-Km-R (SEQ ID NO 17)

gcagaagatggctggcagcgtatgctggaatggtttaagcagtatggtgg gaagaagtcgctgtaaGCAGAAAGGCCCACCCGAAGGTGAGCCAGTGTGA

CATATGAATATCCTCCTTAG with

- a region (lower case) homologous to the sequence (4013377-4013442) of metE region (reference sequence on the website http://www.ecogene.org/),
- a region (upper bold case) for T7te transcriptional terminator sequence (Harrington et al., 2001),
- a region (upper case) for the amplification of the kanamycin resistance cassette (reference sequence in Datsenko & Wanner, 2000.

Kanamycin resistant recombinants were selected and the presence of the Km cassette downstream of the metE gene was verified by PCR with oligonucleotides metE-F and metE-R (described below). The verified and selected strain was called MG1655 metA*11 pKD46 metE::Km.
metE-F (SEQ ID NO 18)

cgtttgggactggatgtgctgg homologous to the sequence (4012495-4012516) of the metE region (reference sequence on the website http://www.ecogene.org/)
metE-R (SEQ ID NO 19)

gcgtggtacggcaaactgac homologous to the sequence (4013672-4013691) of the metE region (reference sequence on the website http://www.ecogene.org/)

The metE::Km chromosomal modification was then transduced into the strain 3, according to Protocol 2.

Kanamycin resistant recombinants were selected and the presence of the Km cassette downstream of the metE gene was verified by PCR with oligonucleotides metE-F and metE-R (described above). The presence of metE gene with the wild type sequence was verified by DNA sequencing.

The resulting strain MG1655 metA*11 metE::Km Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07 was named strain 6.

2. Construction of Strain 7

The plasmid pCL1920-PgapA-pycre-TT07 (described in patent application PCT/FR2010/052937) and the plasmid pCC1BAC-TT02-Ptrc30/RBS01-serC-TT07*2-Ptrc30/RBS01-serA-TTadcca (described above) were introduced into the strain 6, giving the strain MG1655 metA*11 metE::Km Ptrc01*2/RBS08*1-metH Ptrc01-cysPUWAM Ptrc01-cysJIH Ptrc01/RBS01-gcvTHP Ptrc01/ARN01/RBS01-metF Ptrc94-serB ΔmetJ ΔpykF ΔpykA ΔpurU ΔyncA ΔmalS::RN/PRM-CI857-TTadcca-PR01/RBS01*4-thrA*1-cysE ΔpgaABCD::RN/PR01/RBS01-thrA*1-cysE-PgapA-metA*11 ΔuxaCA::RN/PR01/RBS01-thrA*1-cysE-PgapA-metA*11 ΔCP4-6::RN/PR01/RBS01-thrA*1-cysE-PgapA-metA*11 ΔwcaM::RN/PR01/RBS01-thrA*1-cysE-PgapA-metA*11 ΔtreBC::RN/serA-serC ΔyjbI::RN/Ptrc01/RBS01-gcvTHP-TT07 (pCL1920-PgapA-pycre-TT07) (pCC1BAC-TT02-Ptrc30/RBS01-serC-TT07*2-Ptrc30/RBS01-serA-TTadcca), named strain 7.

Measurement of the cobalamin-independent Methionine Synthase (MS, MetE) activity of the strain 6 confirmed that the MetE protein is functional.

Example 4

Production of L-Methionine by Fermentation in Bio-Reactor

Strains that produced substantial amounts of methionine were subsequently tested under production conditions in 0.5 L fermentors (GX, GPC) using a fedbatch strategy.

Briefly, a 24 hours culture grown in 10 mL LB medium with 2.5 g·L$^{-1}$ glucose was used to inoculate a 24 hours preculture in minimal medium (B1a). These incubations were carried out in 500 mL baffled flasks containing 40 mL of minimal medium (B1a) in a rotary shaker (200 RPM). The first preculture was realized at a temperature of 30° C., the second one at a temperature of 34° C.

A third preculture step was carried out in bio-reactors (Sixfors) filled with 200 mL of minimal medium (B1b) inoculated to a biomass concentration of 1.2 g·L$^{-1}$ with 5 mL of concentrated preculture. The preculture temperature was maintained constant at 34° C. and the pH was automatically adjusted to a value of 6.8 using a 10% NH$_4$OH solution. The dissolved oxygen concentration was continuously adjusted to a value of 30% of the partial air pressure saturation with air supply and/or agitation. After glucose exhaustion from the batch medium, the fedbatch was started with an initial flow rate of 0.7 mL·h$^{-1}$ and increased exponentially for 24 hours with a growth rate of 0.13 h$^{-1}$ in order to obtain a final cellular concentration of about 20 g·L$^{-1}$.

TABLE 4

Preculture batch mineral medium composition (B1a and B1b).

| Compound | B1a Concentration (g · L$^{-1}$) | B1b Concentration (g · L$^{-1}$) |
|---|---|---|
| Zn(CH$_3$COO)$_2$•2H$_2$O | 0.0130 | 0.0130 |
| CuCl$_2$•2H$_2$O | 0.0015 | 0.0015 |
| MnCl$_2$•4H$_2$O | 0.0150 | 0.0150 |
| CoCl$_2$•6H$_2$O | 0.0025 | 0.0025 |
| H$_3$BO$_3$ | 0.0030 | 0.0030 |
| Na$_2$MoO$_4$•2H$_2$O | 0.0025 | 0.0025 |
| Fe(III) citrate H$_2$O | 0.1064 | 0.1064 |
| EDTA | 0.0084 | 0.0084 |
| MgSO$_4$•7H$_2$O | 1.00 | 1.00 |
| CaCl$_2$•2H$_2$O | 0.08 | 0.08 |
| Citric acid | 1.70 | 1.70 |
| KH$_2$PO$_4$ | 4.57 | 4.57 |
| K$_2$HPO$_4$•3H$_2$O | 2.50 | 2.50 |
| (NH$_4$)$_2$HPO$_4$ | 1.10 | 1.10 |
| (NH$_4$)$_2$SO$_4$ | 4.90 | 4.90 |
| (NH$_4$)$_2$S$_2$O$_3$ | 1.00 | 1.00 |
| Thiamine | 0.01 | 0.01 |
| Vitamin B12 | 0.01 | 0.01 |
| Glucose | 30.00 | 5.00 |
| MOPS | 30.00 | 0.00 |
| NH$_4$OH 28% | Adjusted to pH 6.8 | Adjusted to pH 6.8 |

TABLE 5

Preculture fedbatch mineral medium composition (F1)

| Compound | Concentration (g · L$^{-1}$) |
|---|---|
| Zn(CH$_3$COO)$_2$•H$_2$O | 0.0104 |
| CuCl$_2$•2H$_2$O | 0.0012 |
| MnCl$_2$•4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0424 |
| EDTA | 0.0067 |
| MgSO$_4$ | 5.00 |
| (NH$_4$)$_2$SO$_4$ | 8.30 |
| Na$_2$SO$_4$ | 8.90 |
| (NH$_4$)$_2$S$_2$O$_3$ | 24.80 |
| Thiamine | 0.01 |
| Glucose | 500.00 |
| Vitamin B12 | 0.01 |
| NH$_4$OH 28% | Adjusted to pH 6.8 |

TABLE 6

Culture batch mineral medium composition (B2).

| Compound | Concentration (g · L$^{-1}$) |
|---|---|
| $Zn(CH_3COO)_2·2H_2O$ | 0.0130 |
| $CuCl_2·2H_2O$ | 0.0015 |
| $MnCl_2·4H_2O$ | 0.0150 |
| $CoCl_2·6H_2O$ | 0.0025 |
| $H_3BO_3$ | 0.0030 |
| $Na_2MoO_4·2H_2O$ | 0.0025 |
| Fe(III) citrate $H_2O$ | 0.1064 |
| EDTA | 0.0084 |
| $MgSO_4·7H_2O$ | 1.00 |
| $CaCl_2·2H_2O$ | 0.08 |
| Citric acid | 1.70 |
| $KH_2PO_4$ | 2.97 |
| $K_2HPO_4·3H_2O$ | 1.65 |
| $(NH_4)_2HPO_4$ | 0.72 |
| $(NH_4)_2S_2O_3$ | 3.74 |
| Thiamine | 0.01 |
| Vitamin B12 | 0.01 |
| Biotin | 0.10 |
| Glucose | 10.00 |
| $NH_4OH$ 28% | Adjusted to pH 6.8 |

TABLE 7

Culture fedbatch medium composition (F2).

| Compound | Concentration (g · L$^{-1}$) |
|---|---|
| $Zn(CH_3COO)_2·2H_2O$ | 0.0104 |
| $CuCl_2·2H_2O$ | 0.0012 |
| $MnCl_2·4H_2O$ | 0.0120 |
| $CoCl_2·6H_2O$ | 0.0020 |
| $H_3BO_3$ | 0.0024 |
| $Na_2MoO_4·2H_2O$ | 0.0020 |
| Fe(III) citrate $H_2O$ | 0.0524 |
| EDTA | 0.0067 |
| $MgSO_4$ | 5.00 |
| $(NH_4)_2S_2O_3$ | 55.50 |
| Thiamine | 0.01 |
| Vitamin B12 | 0.01 |
| Biotin | 0.10 |
| Glucose | 500.00 |

Subsequently, GX 0.5 L fermentors (GPC) were filled with 220 mL of minimal medium (B2) and were inoculated to a biomass concentration of 2.1 g·L$^{-1}$ with a preculture volume ranging between 20 to 30 mL.

The culture temperature was maintained constant at 37° C. and pH was maintained to the working value (6.8) by automatic addition of $NH_4OH$ solutions ($NH_4OH$ 10%). The initial agitation rate was set at 200 RPM during the batch phase and was increased up to 1000 RPM during the fedbatch phase. The initial airflow rate was set at 0.3 L·min$^{-1}$ during the batch phase and was increased up to 0.7 L·min$^{-1}$ at the beginning of the fedbatch phase. The dissolved oxygen concentration was maintained at values between 20 and 40%, preferentially 30% saturation by increasing the agitation.

When the cell mass reached a concentration close to 5 g·L$^{-1}$, the fedbatch was started with an initial flow rate of 1.9 mL·h$^{-1}$. Feeding solution was injected with a sigmoid profile with an increasing flow rate that reached 8.8 mL·h$^{-1}$ after 26 hours. The precise feeding conditions were calculated by the equation:

$$Q(t) = p1 + \frac{p2}{1 + e^{-p3(t-p4)}}$$

where Q(t) is the feeding flow rate in mL·h$^{-1}$ for a batch volume of 600 mL with p1=0.66, p2=8.21, p3=0.27, p4=6.50.

After 26 hours of fedbatch, the feeding solution pump was stopped and the culture was finished after glucose complete exhaustion.

Extracellular amino acids were quantified by HPLC after OPA/Fmoc derivatization and other relevant metabolites were analyzed using HPLC with refractometric detection (organic acids and glucose) and GC-MS after silylation.

TABLE 8

Final methionine yield ($Y_{met\,final}$) in % g of methionine per g of glucose produced in fedbatch culture by the different strains. For the definition of methionine/glucose yield see below. Each strain was evaluated once.

| Strain | $Y_{met\,final}$ |
|---|---|
| Strain 5 | 0.225 |
| Strain 7 | 0.186 |

As can be seen in table 8 above, the yield of methionine production increased significantly upon metE gene mutation. The strain 5, containing the mutated metE gene has a yield higher of 4 points compared to strain 7 which contains a functional MetE protein.

The fermentor volume was calculated by adding to the initial volume of the reactor, the amount of the solutions added to regulate the pH and to feed the culture and by subtracting the volume used for sampling and lost by evaporation.

The fedbatch volume was followed continuously by weighing the feeding stock. The amount of injected glucose was then calculated on the basis of the injected weight, the density of the solution and the glucose concentration determined by the method of Brix ([Glucose]). The methionine yield was expressed as followed:

$$Y_{met} = \frac{Methionine_t * V_t - Methionine_0 * V_0 \times 100}{Consumed\ glucose_t}$$

The final yield obtained during the culture was presented here for each strain. With Methionine$_0$ and Methionine$_t$ respectively the initial and final methionine concentrations and $V_0$ and $V_t$ the initial and the final volumes.

The consumed glucose was calculated as follows:

$$fed\ volume_t = \frac{fed\ weight_0 - fed\ weight_t}{density\ fed\ solution}$$

Injected Glucose$_t$=fed volume$_t$*[Glucose]

Consumed glucose$_t$=[Glucose]$_0$*V$_0$+Injected Glucose−[Glucose]$_{residual}$*V$_t$ With [Glucose]$_0$, [Glucose], [Glucose]$_{residual}$ respectively the initial, the fed and the residual glucose concentrations.

Example 5

Measurement of the Cobalamin-Independent Methionine Synthase (MetE) Activity For the in vitro determination of the cobalamin-independent Methionine Synthase (MS, MetE) activity, *E. coli* strains 7 and 5 carrying wild-type or mutated metE gene respectively were cultured in minimal medium as described in example 3 above and harvested at the end of the log phase by centrifugation. Pellets were resuspended in cold 20 mM potassium phosphate buffer pH 7.2 containing a cocktail of protease inhibitors with EDTA. Then, the cells were broken by bead beating with a Precellys system (Bertin Technologies; 2×10 s at 6500 rpm) followed by centrifugation at 12000 g at 4° C. for 30 minutes. Supernatants were desalted and used for enzymatic analyses. Protein concentrations were determined using Bradford assay reagent (Bradford, 1976).

For the determination of MS activity, 40 µg of crude cell extracts were incubated for 15 minutes at 37° C. with 1 mM DL-homocysteine and 0.25 mM methyl-tetrahydropteroyl-triglutamate in 100 mM potassium phosphate buffer pH7.2, 5 mM MgSO$_4$. The methionine produced by cobalamin-independent Methionine Synthase enzyme was quantified by GC-MS after derivatization with tert-butyldimethylsilyltrifluoroacetamide (TBDMSTFA). Aspartate and Norleucine were included as internal standards.

Results of cobalamin-independent Methionine Synthase activities are presented in table 9 below.

TABLE 9

Cobalamin-independent Methionine Synthase activities (in mUI/mg proteins) of *E. coli* strains carrying wild-type or mutated enzymes. Each strain was evaluated once.

| Strain | MS (mUI/mg proteins) |
|---|---|
| Strain 5 | 0 |
| Strain 7 | 12.7 |

As can be seen in table 9, strain 5 (ΔmetE) has completely lost its MS activity whereas strain 7 kept a significant one. This loss of activity was correlated to a significant improvement of methionine production.

Example 6

Effect of Deletion of Mete Gene on Production of L-Methionine

To evaluate the effect of a complete deletion of the metE gene on the production of L-methionine, we deleted the mutated metE gene of the strain 5. We introduced a clean deletion of metE gene in that strain using the homologous recombination as described previously and using the strategy provided by Datsenko & Wanner (2000).

After replacement of the mutated metE gene by the kanamycin cassette, the kanamycin resistant recombinants are selected and verified by DNA sequencing.

One of them is cultured as described in example 4 and the produced L-methionine is quantified by HPLC.

The strain with the clean deletion of metE produces more methionine than strain 7 which possesses a functional MetE protein: the deletion of metE results in increased yield of methionine of more than 15%.

REFERENCES

Anderson, 1946, *Proc. Natl. Acad. Sci. USA* 32:120-128.
Bradford, 1976, *Anal. Biochem.* 72: 248-254.
Carrier and Keasling, 19981999, *Biotechnol. Prog.* 15: 58-64.
Datsenko and Wanner, 2000, *Proc Natl Acad Sci USA.* 97: 6640-6645.
Foster et al., 1961, *Biochem. J.* 80: 519-531.
Gonzalez et al., 1992, *Biochemistry.* 31: 6045-6056.
Harrington, Laughlin and Liang, 2001 *Proc Natl Acad Sci USA*. April 24; 98(9):5019-24.
Liebl et al., 1989, *Appl. Microbiol. Biotechnol.* 32: 205-210.
Miller, 1992; "*A Short Course in Bacterial Genetics: A Laboratory Manual and Handbook for Escherichia coli and Related Bacteria*", Cold Spring Harbor Laboratory Press, Cold Spring Harbor, N.Y.
Norrander et al., 1983. *Gene.* 26: 101-106.
Orosz et al., 1991, *Eur. J. Biochem.* 201: 653-659
Prescott et al., 1999, "*Microbiology*" 4th Edition, WCB McGraw-Hill.
Riedel et al., 2001, *J. Mol. Microbiol. Biotechnol.* 3: 573-583.
Sambrook et al., 1989 and 2001, "*Molecular Cloning: A Laboratory Manual*" 2nd & 3rd Editions, Cold Spring Harbor Laboratory Press.
Saunderson, 1985 British *Journal of Nutrition* 54: 621-633.
Schaefer et al. 1999, *Anal. Biochem.* 270: 88-96.

The invention claimed is:

1. A recombinant microorganism optimised for the fermentative production of methionine, wherein the activity of the cobalamin-independent methionine synthase MetE is suppressed and the metH gene is overexpressed in said microorganism compared to a non-modified microorganism.

2. The microorganism of claim 1, wherein the cobalamin-independent methionine synthase MetE is encoded by the metE gene of which at least a portion is deleted.

3. The microorganism of claim 2, wherein the deletion of the metE gene is a deletion of the bases comprised between the 417th and 429th positions by reference to the sequence SEQ ID NO: 20.

4. The microorganism of claim 1, wherein the expression of at least one of the following genes is increased: ptsG, pyc, pntAB, cysP, cysU, cysW, cysA, cysM, cysJ, cysI, cysH, gcvT, gcvH, gcvP, lpd, serA, serB, serC, cysE, metF, thrA, metA allele encoding for an enzyme with reduced feed-back sensitivity to S-adenosylmethionine and/or methionine (metA*), thrA, or a thrA allele encoding for an enzyme with reduced feed-back inhibition to threonine (thrA*).

5. The microorganism of claim 4, wherein at least one gene is under the control of an inducible promoter.

6. The microorganism of claim 1, wherein the expression of at least one of the following genes is attenuated: metJ, pykA, pykF, purU, ybdL or yncA.

7. The microorganism of claim 1, wherein:
a. the gene metE is deleted
b. the expression of the genes metA*, cysPUWAM, cysJIH, gcvTHP, metF, serA, serB, serC, cysE, thrA* and pyc are enhanced; and
c. the expression of the genes metJ, pykA, pykF, purU and yncA are attenuated.

8. The microorganism of claim 1, wherein said microorganism is from the bacterial family Enterobacteriaceae or Corynebacteriaceae.

9. The microorganism of claim 1, wherein said microorganism is *Escherichia coli*.

10. A method for the fermentative production of methionine comprising the steps of:
a. culturing a recombinant microorganism according to claim 1 in an appropriate culture medium comprising a fermentable source of carbon and a source of sulphur, and
b. recovering methionine or its derivatives from the culture medium.

11. The method of claim 10 wherein growth of the recombinant microorganism is subjected to limitation or deficiency for one or several inorganic substrate(s), in particular phosphate and/or potassium, in the culture medium.

* * * * *